(12) United States Patent
Banco

(10) Patent No.: US 9,855,361 B2
(45) Date of Patent: Jan. 2, 2018

(54) COMPOSITIONS, DELIVERY SYSTEMS AND REFILLS FOR EMITTING TWO OR MORE COMPOSITIONS

(71) Applicant: S. C. Johnson & Son, Inc., Racine, WI (US)

(72) Inventor: Michael J. Banco, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 69 days.

(21) Appl. No.: 14/967,941

(22) Filed: Dec. 14, 2015

(65) Prior Publication Data

US 2017/0165391 A1 Jun. 15, 2017

(51) Int. Cl.
*A61L 9/012* (2006.01)
*A61L 9/12* (2006.01)

(52) U.S. Cl.
CPC .............. *A61L 9/127* (2013.01); *A61L 9/012* (2013.01)

(58) Field of Classification Search
CPC ...................................................... A61L 9/127
See application file for complete search history.

(56) References Cited

U.S. PATENT DOCUMENTS

| | | | |
|---|---|---|---|
| 3,260,421 A | 7/1966 | Rabussier | |
| 4,767,741 A | 8/1988 | Komor et al. | |
| 6,352,182 B1 | 3/2002 | Gueret | |
| 7,007,863 B2 | 3/2006 | Kotary et al. | |
| 7,281,670 B2 | 10/2007 | Lakatos et al. | |
| 7,548,684 B2 | 6/2009 | Berrido et al. | |
| 7,661,563 B2 | 2/2010 | De Lataulade | |
| 7,867,962 B2 | 1/2011 | Wei et al. | |
| 7,887,759 B2 | 2/2011 | Triplett | |
| 8,084,408 B2 | 12/2011 | Wei et al. | |
| 8,418,933 B2 | 4/2013 | Newman et al. | |

(Continued)

FOREIGN PATENT DOCUMENTS

| | | |
|---|---|---|
| EP | 3120873 | 1/2017 |
| WF | 2014023782 | 2/2014 |

(Continued)

OTHER PUBLICATIONS

Machine Translation of WO 2006038323 A1 dated May 31, 2017 from Patent Scope (WIPO).*

(Continued)

*Primary Examiner* — Lanee Reuther
*Assistant Examiner* — Arrie Lanee Reuther

(57) ABSTRACT

A system for delivering a multi-phase fragrance composition comprises a container having a body forming a reservoir and an opening in communication with the reservoir and a multi-phase composition disposed within the reservoir. The multi-phase composition comprises a water phase composition and an oil phase composition and the water phase composition and the oil phase composition are substantially separated. The water phase composition comprises a water phase fragrance and both water and propylene glycol as water phase solvents. The oil phase composition comprises an oil phase fragrance and isopar M as an oil phase solvent. The system further includes a wick in contact with the water phase composition and the oil phase composition and configured to sequentially emit the water phase composition and the oil phase composition.

11 Claims, 20 Drawing Sheets

(56) References Cited

U.S. PATENT DOCUMENTS

| | | | |
|---|---|---|---|
| RE44,312 E | 6/2013 | Vieira | |
| 8,844,837 B1 * | 9/2014 | Pesu | A61L 9/127 239/289 |
| 8,895,041 B2 | 11/2014 | Scavone et al. | |
| 2001/0006088 A1 | 7/2001 | Lyle | |
| 2002/0179643 A1 | 12/2002 | Knight et al. | |
| 2003/0003069 A1 | 1/2003 | Carson et al. | |
| 2004/0262418 A1 | 12/2004 | Smith et al. | |
| 2007/0117729 A1 | 5/2007 | Taylor et al. | |
| 2007/0280976 A1 | 12/2007 | Taylor et al. | |
| 2009/0029900 A1 | 1/2009 | Cetti et al. | |
| 2014/0249064 A1 | 9/2014 | Scavone et al. | |
| 2014/0329735 A1 | 11/2014 | Bara | |
| 2015/0045275 A1 | 2/2015 | Scavone et al. | |

FOREIGN PATENT DOCUMENTS

| | | | |
|---|---|---|---|
| WO | 2004032983 | 4/2004 | |
| WO | 2006038323 | 4/2006 | |
| WO | WO 2006038323 A1 * | 4/2006 | A61L 9/127 |
| WO | 2009087118 | 7/2009 | |
| WO | 2014023782 A1 | 2/2014 | |
| WO | 2016044043 | 3/2016 | |

OTHER PUBLICATIONS

Product Data Sheet Isopar M from ExxonMobil. Obtained May 31, 2017 from https://www.exxonmobilchemical.com/Chem-English/Files/Resources/isopar-m-fluid-product-safety-summary.pdf.*

International Search Report and Written Opinion issued in corresponding PCT Application No. PCT/US2016/062062, dated Mar. 1, 2017, 12 pages.

* cited by examiner

C1 - Formula 1

| 40% Total Fragrance Load and 20% Water | | | | | |
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | Dimethyl Adipate | LVP | 627-93-0 | 1.6 | 10 |
| Oil Phase Fragrance | Fruity Oil 059FR | | | 3.2 | 20 |
| Water Phase Solvent | Propylene Glycol | N | 57-55-6 | 3.2 | 20 |
| Water | Water | N | | 3.2 | 20 |
| Water Phase Fragrance | Fresh Floral Water 0352BX | | | 3.2 | 20 |
| | | | Totals | 16 | 100 |

C2 - Formula 2

| 40% Total Fragrance Load and 20% Water | | | | | |
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | Hexyl Cellosolve | N | 112-25-4 | 1.6 | 10 |
| Oil Phase Fragrance | Fruity Oil 059FR | | | 3.2 | 20 |
| Water Phase Solvent | Propylene Glycol | N | 57-55-6 | 3.2 | 20 |
| Water | Water | N | | 3.2 | 20 |
| Water Phase Fragrance | Fresh Floral Water 0352BX | | | 3.2 | 20 |
| | | | Totals | 16 | 100 |

C3 - Formula 3

| 50% Total Fragrance Load and 20% Water | | | | | |
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | None | | | 0 | 0 |
| Oil Phase Fragrance | Fruity Oil 059FR | | | 4.8 | 30 |
| Water Phase Solvent | Propylene Glycol | N | 57-55-6 | 3.2 | 20 |
| Water | Water | N | | 3.2 | 20 |
| Water Phase Fragrance | Fresh Floral Water 0352BX | | | 3.2 | 20 |
| | | | Totals | 16 | 100 |

FIG. 19

C4 - Formula 4

| 40% Total Fragrance Load and 15% Water ||||||
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | Dimethyl Adipate | LVP | 627-93-0 | 1.6 | 10 |
| Oil Phase Fragrance | Fruity Oil 059FR | | | 3.2 | 20 |
| Water Phase Solvent | Propylene Glycol | N | 57-55-6 | 4.0 | 25 |
| Water | Water | N | | 2.4 | 15 |
| Water Phase Fragrance | Fresh Floral Water 0352BX | | | 3.2 | 20 |
| | | | Totals | 16 | 100 |

C5 - Formula 5

| 40% Total Fragrance Load and 15% Water ||||||
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | Hexyl Cellosolve | N | 112-25-4 | 1.6 | 10 |
| Oil Phase Fragrance | Fruity Oil 059FR | | | 3.2 | 20 |
| Water Phase Solvent | Propylene Glycol | N | 57-55-6 | 4.0 | 25 |
| Water | Water | N | | 2.4 | 15 |
| Water Phase Fragrance | Fresh Floral Water 0352BX | | | 3.2 | 20 |
| | | | Totals | 16 | 100 |

C6 - Formula 6

| 50% Total Fragrance Load and 15% Water ||||||
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | None | | | 0 | 0 |
| Oil Phase Fragrance | Fruity Oil 059FR | | | 4.8 | 30 |
| Water Phase Solvent | Propylene Glycol | N | 57-55-6 | 4.0 | 25 |
| Water | Water | N | | 2.4 | 15 |
| Water Phase Fragrance | Fresh Floral Water 0352BX | | | 3.2 | 20 |
| | | | Totals | 16 | 100 |

FIG. 19 (Cont.)

C7 - Formula 7

| 40% Total Fragrance Load and 10% Water | | | | | |
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | Dimethyl Adipate | LVP | 627-93-0 | 1.6 | 10 |
| Oil Phase Fragrance | Fruity Oil 059FR | | | 3.2 | 20 |
| Water Phase Solvent | Propylene Glycol | N | 57-55-6 | 4.8 | 30 |
| Water | Water | N | | 1.6 | 10 |
| Water Phase Fragrance | Fresh Floral Water 0352BX | | | 3.2 | 20 |
| | | | Totals | 16 | 100 |

C8 - Formula 8

| 40% Total Fragrance Load and 10% Water | | | | | |
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | Hexyl Cellosolve | N | 112-25-4 | 1.6 | 10 |
| Oil Phase Fragrance | Fruity Oil 059FR | | | 3.2 | 20 |
| Water Phase Solvent | Propylene Glycol | N | 57-55-6 | 4.8 | 30 |
| Water | Water | N | | 1.6 | 10 |
| Water Phase Fragrance | Fresh Floral Water 0352BX | | | 3.2 | 20 |
| | | | Totals | 16 | 100 |

C9 - Formula 9

| 50% Total Fragrance Load and 10% Water | | | | | |
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | None | | | 0 | 0 |
| Oil Phase Fragrance | Fruity Oil 059FR | | | 4.8 | 30 |
| Water Phase Solvent | Propylene Glycol | N | 57-55-6 | 4.8 | 30 |
| Water | Water | N | | 1.6 | 10 |
| Water Phase Fragrance | Fresh Floral Water 0352BX | | | 3.2 | 20 |
| | | | Totals | 16 | 100 |

FIG. 20

C10 - Formula 10

| 40% Total Fragrance Load and 5% Water | | | | | |
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | Dimethyl Adipate | LVP | 627-93-0 | 1.6 | 10 |
| Oil Phase Fragrance | Fruity Oil 059FR | | SCJ 115302 | 3.2 | 20 |
| Water Phase Solvent | Propylene Glycol | N | 57-55-6 | 5.6 | 35 |
| Water | Water | N | | 0.8 | 5 |
| Water Phase Fragrance | Fresh Floral Water 0352BX | | SCJ 115301 | 3.2 | 20 |

Totals 16 100

C11 - Formula 11

| 40% Total Fragrance Load and 5% Water | | | | | |
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | Hexyl Cellosolve | N | 112-25-4 | 1.6 | 10 |
| Oil Phase Fragrance | Fruity Oil 059FR | | SCJ 115302 | 3.2 | 20 |
| Water Phase Solvent | Propylene Glycol | N | 57-55-6 | 5.6 | 35 |
| Water | Water | N | | 0.8 | 5 |
| Water Phase Fragrance | Fresh Floral Water 0352BX | | SCJ 115301 | 3.2 | 20 |

Totals 16 100

C12 - Formula 12

| 50% Total Fragrance Load and 5% Water | | | | | |
|---|---|---|---|---|---|
| Chemical Purpose | Chemical | VOC? | CAS# | Grams in 16g Fill | Wt% |
| Oil Phase Solvent #1 | Isopar M | N | 64742-47-8 | 1.6 | 10 |
| Oil Phase Solvent #2 | None | | | 0 | 0 |
| Oil Phase Fragrance | Fruity Oil 059FR | | SCJ 115302 | 4.8 | 30 |
| Water Phase Solvent | Propylene Glycol | N | 57-55-6 | 5.6 | 35 |
| Water | Water | N | | 0.8 | 5 |
| Water Phase Fragrance | Fresh Floral Water 0352BX | | SCJ 115301 | 3.2 | 20 |

Totals 16 100

FIG. 20 (Cont.)

COMPOSITIONS, DELIVERY SYSTEMS AND REFILLS FOR EMITTING TWO OR MORE COMPOSITIONS

BACKGROUND

1. Field of the Disclosure

The present disclosure relates generally to compositions, delivery systems and refills for sequentially emitting two or more compositions.

2. Description of the Background

It is known that the perception of a user of a dispensed fragrance at a constant delivery rate tends to decay over time. This decay in perception, which is commonly referred to as adaptation and/or habituation, reduces the enjoyment of the dispensed fragrance by the user. Adaptation and/or habituation are the reduction of physiological, psychological, or behavioral response occurring when a specific stimulus occurs repeatedly. It is generally believed that adaptation and/or habituation with respect to a fragrance can be reduced by changing the level of intensity of the dispensed fragrance or by dispensing a different fragrance. Fragrance dispensers and methods of dispensing fragrances that address the issue of adaptation and/or habituation are known in the art.

One such fragrance dispenser emits a first fragrance from a first refill for a first period of time followed by emission of a second fragrance from a second refill for a second period of time followed by emission of a third fragrance from a third refill for a third period of time. A further pattern or algorithm for dispensing fragrances includes emission of a first fragrance from a first refill in repeated short intermittent bursts during a first period of time, the emission of a second fragrance from a second refill in repeated short intermittent bursts during a second period of time, and the emission of a third fragrance from a third refill in repeated short intermittent bursts during a third period of time. In any of the above-described patterns or algorithms, one or more fans, heaters, or any suitable devices may be utilized to facilitate emission of each of the fragrances.

Another dispenser emits fragrances in an alternating sequence while the dispenser is activated. The dispenser includes, for example, first and second heaters for emitting first and second fragrances, respectively, from first and second refills, respectively. In one embodiment, the fragrances are alternatively emitted by deactivating one of the heaters at the same time the other of the heaters is activated. Alternatively, one of the heaters may be deactivated followed by a gap period and then the other of the heaters may be activated. Still further, one of the heaters may be activated before the other of the heaters is deactivated to create an overlap period. Existing devices offering solutions to adaptation and/or habituation may change dispensed fragrances or intensities thereof frequently over a period of a day or several hours, for example, every 45 minutes, thereby exposing a user to a seemingly constant change of fragrance.

Current multi-fragrancing devices require multiple refills and/or multiple actuators for emitting different fragrances. Multiple refills and/or multiple actuators increase the footprint and/or overall size of a dispenser from which the fragrances are emitted and/or increase the overall cost of the dispenser.

Fragrance compositions used in air fresheners are composed of a mixture of volatile Perfume Raw Materials. It is not uncommon for a fragrance composition to be composed of over 20 different Perfume Raw Materials. The chemical properties of Perfume Raw Materials in a fragrance composition often vary widely in terms of polarity, density, vapor pressure, flash point, and other properties. However, all Perfume Raw Materials must have sufficient vapor pressure to be volatilized into the air in order for human olfactory perception to occur.

Fragrance compositions that are delivered into the air evaporatively (such as by plug-in type air fresheners that evaporate a fragrance composition into the air from a heated wick) do not deliver the fragrance composition into the air in an uniform manner. Instead, the more volatile components of the fragrance composition dominate the composition that evaporates at first. As such, over time, the composition of the evaporating fragrance composition becomes more concentrated with the less volatile Perfume Raw Materials in the composition. Perfumers have learned to create fragrance compositions that partially compensate for this change in fragrance composition over time by selecting Perfume Raw Materials that will maintain a consistent olfactory experience as much as possible, even though the fragrance composition is changing over time.

It would be useful if perfumers could overcome the limitation that the more volatile ingredients in a fragrance composition are exhausted from the fragrance composition more quickly than the less volatile components of the fragrance composition in an evaporation-based fragrance delivery system (such as plug-in air fresheners).

SUMMARY

In an illustrative embodiment, a method of emitting a multi-phase composition from a delivery system comprises a container having a body forming a reservoir and an opening in communication with the reservoir and a multi-phase composition disposed within the reservoir. The multi-phase composition comprises a water phase composition and an oil phase composition, wherein the water phase composition and the oil phase composition are substantially separated and the water phase composition has a different fragrance characteristic than the oil phase composition. The water phase composition comprises a water phase fragrance and both water and a water-soluble solvent as water phase solvents, and the oil phase composition comprises an oil phase fragrance and an oil-soluble solvent as an oil phase solvent. A wick is in contact with the water phase composition and the oil phase composition and configured to sequentially emit the water phase composition and the oil phase composition. The method comprises the steps of emitting one of the water and oil phase compositions until the one of the water and oil phase compositions is substantially depleted and emitting the other of the water and oil phase compositions after the one of the water and oil phase compositions is substantially depleted.

In some embodiments, a delivery system for delivering a multi-phase fragrance composition comprises a container having a body forming a reservoir and an opening in communication with the reservoir and a multi-phase composition disposed within the reservoir. The multi-phase composition comprises a water phase composition and an oil phase composition and the water and oil phase compositions are substantially separated. The water phase composition comprises a water phase fragrance and both water and a water-soluble solvent as water phase solvents and the oil phase composition comprises an oil phase fragrance and an oil-soluble solvent as an oil phase solvent. A wick is in contact with the water and oil phase compositions and is configured to sequentially emit the water and oil phase compositions.

BRIEF DESCRIPTION OF THE DRAWINGS

FIG. 19 are tables showing exemplary formulas 1 through 6 (samples C1-C6); and

FIG. 20 are tables showing exemplary formulas 7 through 12 (samples C7-C12).

Other aspects and advantages of the present disclosure will become apparent upon consideration of the following detailed description, wherein similar structures have like or similar reference numerals.

DETAILED DESCRIPTION

The present application is directed to volatile material compositions, delivery systems, and refills for such compositions and methods of sequentially emitting two or more compositions from the delivery systems and refills. While the present application may be embodied in many different forms, several specific embodiments are discussed herein with the understanding that the present application is to be considered only as an exemplification of the principles of the application, and it is not intended to limit the application to the embodiments illustrated.

In one aspect, the present application discloses a delivery system and refill for dispensing volatile materials. In one embodiment, the volatile materials include two or more phases. In an exemplary embodiment, the volatile materials include two phases.

In some embodiments, the present application is a delivery system that is capable of delivering a multi-phase solution of volatile material compositions in a phase-by-phase manner. In one exemplary embodiment, the delivery system includes a refill having a wick assembly in a reservoir. The wick assembly may allow multiple phases of the multi-phase composition of volatile materials to enter the wick at the same time. In one embodiment, the wick assembly may allow one certain phase of the multi-phase composition to selectively enter the wick. In one embodiment, the wick assembly may allow the phase of the multi-phase volatile composition at the bottom of the reservoir to selectively enter the wick. In another embodiment, the wick assembly may allow any phase of the multi-phase compositions that is not at the bottom of the reservoir to selectively enter the wick.

In the following examples, a wick assembly that allows the phase of the multi-phase composition at the bottom of the reservoir to selectively enter the wick is depicted. However, Applicants envision that the present application is also applicable to a wick assembly that allows the phase of the multi-phase composition that is not at the bottom of the reservoir to selectively enter the wick.

Further, in the following examples, a two-phase composition of volatile materials is used for the purpose of demonstration. Applicants envision that the present application is also applicable to any multi-phase composition of volatile materials.

Figure 1:
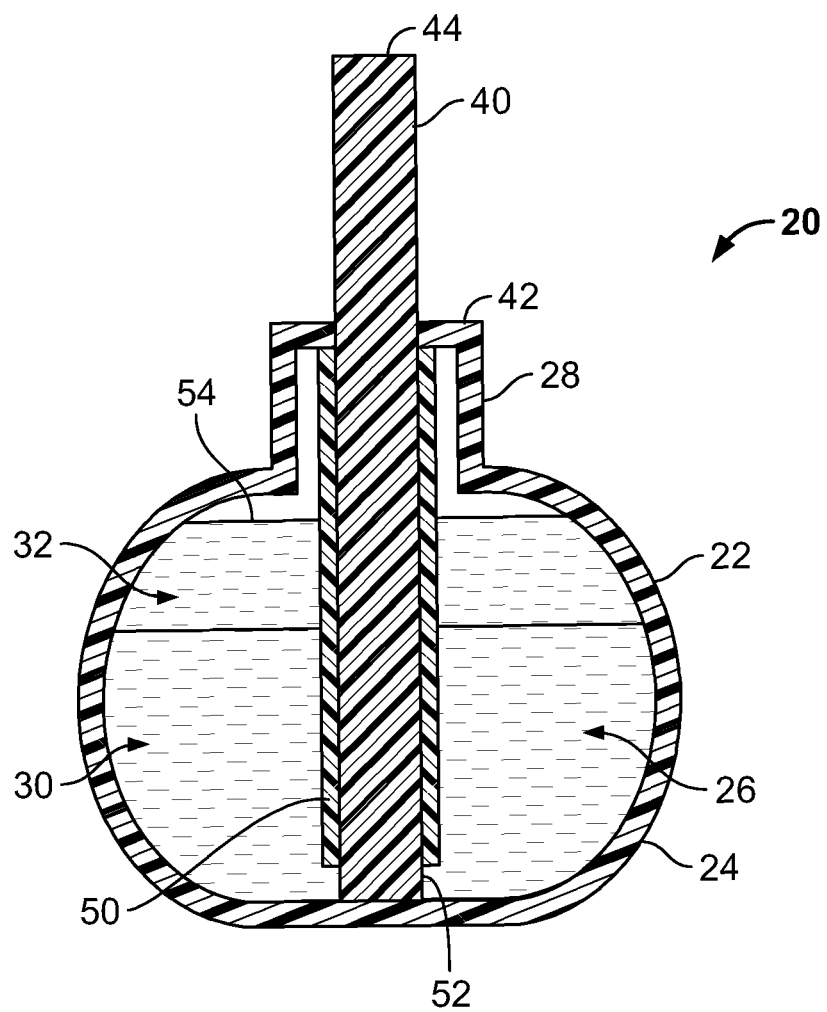
FIG. 1 is a cross-sectional view of a first embodiment of a refill including a container having a reservoir holding first and second compositions and a wick in contact with the first and second compositions and extending out of the refill.

Referring to the drawings, FIG. 1 depicts a first embodiment of a delivery system and refill 20 of the present disclosure. The delivery system and refill 20 may include a container 22 including a body 24 having a reservoir 26 for holding a multi-phase liquid (e.g., a two-phase liquid). The container 22 may further include a hollow neck 28 extending from the body 24 and in communication with the reservoir 26. The container 22 may be made of plastic or any other suitable material. Further, while the delivery system and refill 20 are depicted as having a particular configuration, the principles of the present disclosure may be utilized in conjunction with any suitable refill.

Two or more different compositions (e.g., a multi-phase composition) may be held within the reservoir 26 of the container 22, as seen in FIG. 1. For example, a two-phase composition may include a first composition 30 and a second composition 32 that may be layered within the reservoir 26, for example, with the first composition 30 below the second composition 32. In the embodiments disclosed herein, the first and second compositions 30, 32 may be sequentially emitted with the first composition 30 emitted first and the second composition 32 emitted second or the second composition 32 emitted first and the first composition 30 emitted second.

The first and/or second compositions 30, 32 may be any suitable liquid or liquids and one or both of the compositions 30, 32 may include one or more active ingredients. Exemplary active ingredients include, but are not limited to, one or more of a cleaner, an insecticide, an insect repellant, an insect attractant, a disinfectant, a mold or mildew inhibitor, an antimicrobial, a fragrance comprised of one or more aroma chemicals, a disinfectant, an air purifier, an aromatherapy scent, an antiseptic, an odor eliminator, a positive fragrancing active material, an air-freshener, a deodorizer, a medicinal component, an inhalant (e.g., for relieving a cough or congestion), or the like, and combinations thereof. Regardless of the specific compositions, the first and second compositions 30, 32 may be the same or different. The first and second compositions also form a two-phase liquid wherein each of the compositions forms a separate layer within the delivery system and refill 20, such that the two compositions are sequentially emitted.

In one embodiment, the active ingredients are fragrances. The term "fragrance," as used herein, refers to any substance or a mixture of substances such as a perfume designed to emit an aromatic and pleasant scent. A wide variety of chemicals are known for fragrance (i.e., perfume) uses, including materials such as aldehydes, ketones and esters. More commonly, naturally occurring plant and animal oils and exudates comprising complex mixtures of various chemical components are known for use as fragrances.

In one embodiment, the fragrances of the present application may comprise a single chemical or may comprise highly sophisticated complex mixtures of natural and synthetic chemical components, all chosen to provide any desired odor. For example, the fragrances of the present application may comprise one or more perfume raw materials. The term "perfume raw materials," as used herein, refers to any compound (e.g., those having molecular weight of at least 100 g/mol) or substance that are useful in imparting an odor, fragrance, essence, or scent either alone or in combination with other "fragrance raw materials." Mixture of fragrance raw materials are known by those skilled in the art of fragrances and perfumes as "accords." The term "accord," as used herein, refers to a mixture of two or more fragrance raw materials which are artfully combined to impart a pleasurable scent, odor, essence, or fragrance characteristic.

In one embodiment, the perfume raw materials of the present multi-phase compositions may have boiling points (BP) of about 500° C. or lower, about 400° C. or lower, about 350° C. or lower, or about 300° C. or lower. The BP of many perfume raw materials are given in Perfume and Flavor Chemicals (Aroma Chemicals), Steffen Arctander (1969). The ClogP value of the perfume raw materials useful herein may preferably be greater than about 0.1, greater than about 0.5, greater than about 1.0, or greater than about 1.2. In one embodiment, the ClogP value of the perfume raw materials useful herein may be in the range of about 0.1 to about 2.9, in the range of about 0.2 to about 2.5, or in the range of about 0.5 to about 2.4.

Figure 10:
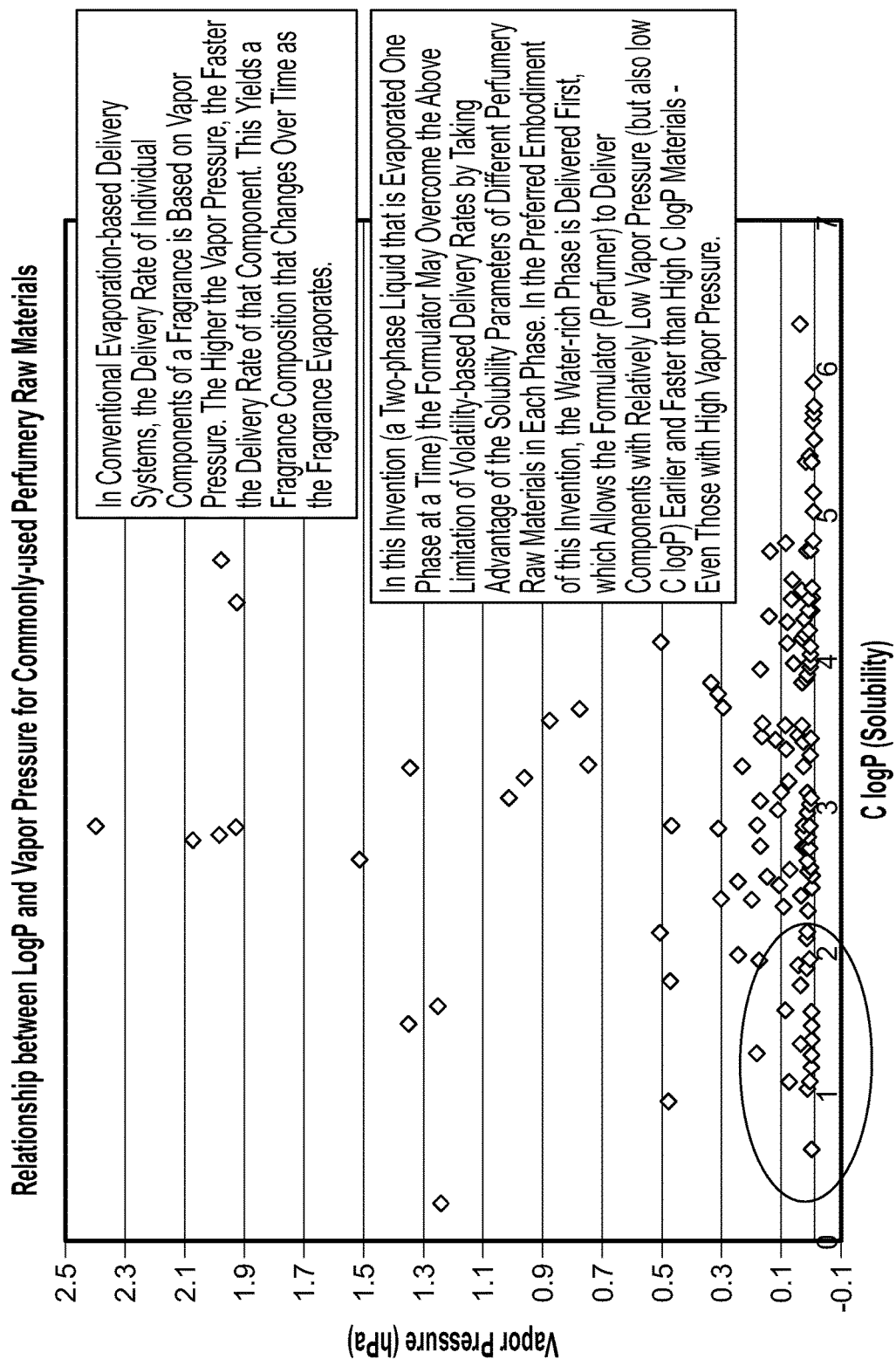
FIG. 10 is a graph depicting a relationship between ClogP and vapor pressure for commonly-used perfume raw materials.

In one embodiment, the perfume raw materials of the present compositions may have any suitable vapor pressure as appreciated by one skilled in the art. FIG. 10 depicts a relationship between ClogP and vapor pressure for commonly-used perfume raw materials. Applicants note that the delivery rate of individual components of a fragrance is based on vapor pressure in conventional evaporation-based delivery systems. The higher the vapor pressure, the faster the delivery rate of that component. Thus, the fragrance composition of a conventional evaporation-based delivery system changes over time as the fragrance evaporates.

In one embodiment, the multi-phase composition and the unique wick assembly of the present application allow the multi-phase compositions to evaporate one phase at one time. As such, the present application overcomes the limitation of the conventional evaporation-based delivery systems (i.e., volatility-based delivery rates) by taking advantage of the solubility parameters of different perfume raw materials in each phase. In some embodiments, a water-rich phase may be delivered first, which allows the formulator to deliver components with relatively low vapor pressure and low ClogP earlier and faster than high ClogP materials (including those with high vapor pressure).

Perfume raw materials that can be used in the present application may include, but are not limited to, ethyl 2,4 decadienoate, allyl heptoate, amyl acetate, ethyl butyrate, Grapefruit Zest (C&A), prenyl acetate, pinoacetaldehyde, 2,6-nonadienol, 3,6-nonadienol, cis-6-nonenol, excital, ebanol, polysantol, orange juice carbonyls, lemon juice carbonyls, orange sinensal, paradiff, tangerinal, benzaldehyde, mandarin aldehyde, undecalactone, norlimbanol, decyl aldehyde, trans-2-hexenal, trans-2-decenal, damascenone, 2-isobutylthiazole, 4-methyl-4-mercaptopentan-2-one, corps cassis 0.1% TEC, patchouli, 2-methoxy-4-vinylphenol, pyridine acetyl 10%, sulfurol, diacetyl, furaneol, maple lactone, allyl amyl glycolate, Ambroxan, alpha damascone damascene, Cetalox, cyclal C, Cedramber, cyclo galbanate, Galbex, Cymal, nerol, Florhydral, P.t. bucinal, iso cyclo citral, Fructone, methyl iso butenyl tetrahydro pyran, Frutene, Delphone, ethyl methyl phenyl glycidate, Violiff, for acetate, Delta damascone damascene, Ambrox, Calone, iso eugenol, Hivernal, methyl beta napthyl ketone, Ozonil, benzyl salicylate, Spirogalbone, cinnamic alcohol, Javanol, dihydro iso jasmonate, Adoxal, Kharismal, pyrazines, ethyl anthranilate, aldehyde supra, Bacdanol, Anethol, irisantheme, yara yara, Keone, cis 3 hexenyl salicylate, methyl nonyl ketone, coumarin, gamma dodecalactone, Applinate, eucalyptol, intreleven aldehyde, heliotropin, indol, Manzanate, ionone, alpha, trans 4 decenal, ionone beta, Oxane, neobutanone, Clonal, methyl octine carbonate, Floralozone, methyl heptine carbonate, methyl nonyl acetaldehyde, Cashmeran, phenoxy ethyl iso butyrate, phenyl acetaldehyde, ethyl methyl phenyl glycidate, undecyl aldehyde, Aurantiol, nectaryl, buccoxime, Laurie aldehyde, nirvanol, Trifernal, pyrazobutyle, Veloutone, Anisic aldehyde, paramenthene, isovaleric aldehyde 0.1% DPG, liminal, labienoxime, rhubofix, iso propyl quinoline, 4-(2,6,6-Trimethyl-1-cyclohexenyl)-3-butenone-2; (3 aR-(3 aalpha,5abeta, 9aalpha, 9bbeta))-dodecahydro-3a,6,6,9a-tetramethyl naphtha(2,1-b) furan; 2,6-Dimethyl-5-heptenal; 3,7-Dimethyl-1,6-octadien-3-ol; 3-Methyl-2-buten-1-yl acetate; 3,7-Dimethyl-2,6-octadienenitrile; 2,4-Dimethylcyclohexene-3-carbaldehyde; Phenyl Acetaldehyde, Indol, ethyl methyl dioxolane acetate; 4-(2,6,6-Trimethyl-1,3-cyclohexadienyl)-3-buten-4-one; Cis-3-Hexenyl Acetate; Laurie Aid, Tricyclo decenyl acetate, Para cresyl methyl ether, 7-acetyl, 1,2,3,4,5,6,7,8-octahydro-1,1,6,7-tetramethyl naphthalene; 3-buten-2-one; 3-methyl-4-(2,6,6-trimethyl-2-cyclohexen-1-yl); Acetic acid (Cyclohexyloxy), 2-propenyl ester; 3-buten-2-one, 4-(2,6,6-trimethyl-2-cyclohexen-1-yl), (E); Decyl Aldehyde, Methyl-3,4-dioxy(cylcoacetonyl) benzene; 2,6-Dimethyl-2,6-octadien-8-ol; ortho tertiary butyl cyclohexanyl acetate; Hexanoic acid,2-propenyl ester; Methoxybenzaldehyde; 3-(3-Isopropylphenyl)butanal; Iso-2-Methoxy-4-(2-propenyl)phenol, Tetra Hydro 3,7-Dimethyl-1,6-octadien-3-ol;

1-methyl-4-isopropenyl-1-cyclohexene; Methyl phenyl carbonyl acetate; Hexahydro-4,7methano-1H-inden-5(or 6)-yl propionate; Benzaldehyde, 3,7-Dimethyl-2,6-octadienal; 3,3-Dimethyl-5-(2,2,3-trimethyl-3-cycloenten-1-yl)-4-penten-2-ol; 2-Methoxy-4-(2-propenyl)phenol; 3,7-dimethyl-6-octen-1-ol; Allyl heptanoate; 1,3-Oxathiane, 2-methyl-4-propyl-, cis-paradiff; (all-E)-alpha-sinensal, 2,6,10-trimethyl-2(E),6(E),9(E),1,1-dodecatetraenal; mandarin aldehyde, p-1-menthen-8-thiol; 4-Methyl-3-decen-5-ol; Ethyl caproate, Ethyl-2-4-decadienoate, 4-Penten-1-one, 1-(5,5-Dimethyl-1-cyclohexen-1-yl)-; 1H-Indene-a-propanal, 2,3-dihydro-1,1-dimethyl-(9Cl); Methyl nonyl acetaldehyde; Orange juice Carbonyls; 4-dodecenal; 3-cyclohexene-1-carboxaldehyde, 2,4-dimethyl; 2,6-nonenol; 2,6-nonadeinal; 2,6-nonadienol; 3-p-cumenyl-propionaldehyde 4-(1-methylethyl)-benzenepropanal; 1-(2,6,6-Trimethyl-1,3-cyclohexandienyl)-2-buten-1-one; 6-(Z,3-pentenyl)-tetrahydro-(2H)-pyranone-2; 3-Methyl-(cis-2-penten-1-yl)-2-cyclopenten-1-one-2,6-nonenol; 2,6-nonadienol; (3aR-(3aalpha,5abeta,9aalpha,9bbeta))-dodecahydro-3a,6,6,9a-tetramethyl naphtha(2,1-b)furan; Beta Gamma Hexenol; Cis-3-hexenyl acetate; 3-P-cumenyl-propionaldehyde-4-(1-methylethyl)-benzenepropanal; 1-(2,6,6-Trimethyl-1,3-cyclohexandienyl)-2-buten-1-one; 3-(3-Isopropylphenyl)butanal; 4-Penten-1-one, 1-(5,5-Dimethyl-1-cyclohexen-1-yl)-; 1H-Indene-a-propanal, 2,3-dihydro-1,1-dimethyl-(9CI) 4-(2,6,6-Trimethyl-1-cyclohexenyl)-3-butenone-2; 6-(Z,3-pentenyl)-tetrahydro-(2H)-pyranone-2; 2,6-Dimethyl-5-heptenal; 6,6-Dimethylbicyclo{3.1.1}Hept-2-ene-2-proponal; 3-cyclohexene-1-carboxaldehyde, 2,4-dimethyl; 4-Methyl-3-decen-5-ol; ortho tertiary butyl cyclohexanyl acetate; 3-Methyl-(cis-2-penten-1-yl)-2-cyclopenten-1-one; 4-Pentene-2-ol, 3,3-dimethyl-5-(2,2,3-trimethyl-3-cyclopenten-1-yi)-. Benzaldehyde; Undeclactone; 4-(2,6,6-Trimethyl-1-cyclohexenyl)-3-butenone-2; allyl heptanoate; 1,3-Oxathiane, 2-methyl-4-propyl-, cis-; Paradiff, (all-E)-alpha-sinensal, 2,6,10-trimethyl-2(E),6(E),9(E),-1,1-dodecatetraenal; mandarin aldehyde; 4-dodecenal; p-1-menthen-8 thiol; Orange Juice Carbonyls; decyl aldehyde; 4-Methyl-3-decen-5-ol; 4-Penten-1-one, 1-(5,5-Dimethyl-1-cyclohexen-1-yl)-Hexanoic acid,2-propenyl ester; 4-Methoxybenzaldehyde; Allyl Heptanoate; Benzaldehyde; 1,3-Oxathiane, 2-methyl-4-propyl-, cis-; decyl aldehyde; Ethyl 2'4-decadienoate; Ethyl Caproate; 4-Penten-1-one, 1-(5,5-Dimethyl-1-cyclohexen-1-yl)-; p-1-menthen-8 thiol; (all-E)-alpha-sinensal 2,6,10-trimethyl-2(E),6(E),9(E),11-dodecatetraenal; IH-Indene-a-propanal, 2,3-dihydro-1,1-dimethyl-(9Cl); 4-(2,6,6-Trimethyl-1-cyclohexenyl)-3-butenone-2; 3 dodecenal; Methyl Nonyl Acetaldehyde; Orange Juice Carbonyls; Paradiff; 4 dodecenal; 3-cyclohexene-1-carboxaldehyde, 2,4-dimethyl; 4-Methyl-3-decen-5-ol; animal fragrances such as musk oil, civet, castoreum, ambergris; plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract, acetophenone, adoxal, aldehyde C-12, aldehyde C-14, aldehyde C-18, allyl caprylate, allyl heptanoate, ambroxan, dimethylindane derivatives, anethole, anisaldehyde, benzaldehyde, benzyl acetate, benzyl alcohol and ester derivatives, benzyl propionate, benzyl salicylate, beta gamma hexanol, borneol, butyl acetate, camphor, carbitol, carvone, cetalox, cinnamaldehyde, cinnamyl acetate, cinnamyl alcohol, cis-3-hexanol and ester derivatives, cis-3-hexenyl methyl carbonate, cis jasmone, citral, citronnellol and ester derivatives, cumin aldehyde, cyclamen aldehyde, cyclo galbanate, damascones, decanol, decyl aldehyde, estragole, delta muscenone, dihydromyrcenol, dimethyl benzyl carbinol, 6,8-dimethyl-2-nonanol, dimethyl benzyl carbinyl butyrate, ethyl isobutyrate, ethyl propionate, ethyl caprylate, ethyl cinnamate, ethyl hexanoate, ethyl valerate, exaltolide, fenchone, galaxolide, geraniol and ester derivatives, hedione, helional, 2-heptonone, hexenol, hexyl salicylate, hydroxycitrolnellal, ionones, isoeugenol, isoamyl iso-valerate, iso E super, linalool acteate, lilial, lyral, majantol, mayol, menthol, p-methylacetophenone, methyl cedrylone, methyl dihydrojasmonate, methyl eugenol, mugetanol, para hydroxy phenyl butanone, phenoxynol, phenyl-acetaldehyde dimethyl acetate, phenoxyethyl isobutyrate, phenyl ethyl alcohol, pinenes, sandalore, sanjinol, santalol, thymol, terpenes, tonalide, 3,3,5-trimethylcyclohexanol, undecylenic aldehyde, phenyl ethyl alcohol, linalool, geraniol, citronellol, cinnamic alcohol, iso bornyl acetate, benzyl acetate, para-tertiarybutyl cyclohexyl acetate, linalyl acetate, dihydro-nor-dicyclopentadienyl acetate, dihydro-nor-dicyclopentadienyl propionate, amyl salicylate, benzyl salicylate, para-iso-propyl alpha-octyl hydrocinnamic aldehyde, hexyl cinnamic aldehyde, hydroxy citronellal, heliotropin, anisaldehyde, citral, dextro limonene, coumarin, ionone gamma methyl, methyl beta naphthyl ketone, gamma undecalactone, eugenol, musk xylol, 1,3,4,6,7,8-hexahydro-4,6,6,7,8,8-hexamethylcyclopenta-gamma-2-benzopyrane, 4-acetyl-6-tertiarybutyl-1,1-dimethyl indan, 6-acetyl-1,1,3,4,4,6-hexamethyl tetrahydro naphthalene, beta naphthyl ethyl ether, methyl eugenol, methyl cedrenyl ketone, patchouli, lavandin, geranyl nitrile, alpha ionone, alpha beta ionone, benzyl iso eugenol, amyl cinnamic aldehyde, beta gamma hexenol, orange CP, ortho-tertiary-butyl cyclohexyl acetate, 2-methyl-3-(para-iso-propylphenyl)propionaldehyde, trichloro methyl phenyl carbinyl acetate, nonane diol-1,3-acetate, methyl dihydro jasmonate, phenoxy ethyl iso butyrate, citronella, citronellal, citrathal, tetrahydromuguol, ethylene brassylate, musk ketone, musk tibetine, phenyl ethyl acetate, oakmoss 25%, hexyl salicylate, eucalyptol, Stemone, Cashmeran, GERANIOL, Citronellyl nitrile, Linalool, Ethyl linalool, Benzyl acetate, Undecavertol, Methyl Phenyl Carbinyl Acetate, 6-Nonen-1-ol, (6Z)-, Benzyl propionate, Iso-E Super, 2,6-Nonadien-1-ol, (2E,6Z)-(10% Nonadienol in DPG), cis-3-Hexen-1-ol (beta gamma hexenol), Isobornyl acetate, Ambrox DL, ozone propanal (Floralozone), 3-methyl-5-(2,2,3-trimethyl-3-cyclopenten-1-yl)pent-4-en-2-ol (Ebanol), Phenethyl isobutyrate, Florhydral, phenyl ethyl alcohol, bourgeonal, gamma-Undecalactone (racemic), Dihydromyrcenol, Ethyl 2-methyl-1,3-dioxolane-2-acetate (Fructone), Bigarade oxide, Allyl cyclohexyl propionate, Tetrahydrolinalool (Tetrahydro Linalool), Trimofix O, Citronellol, Neofolione, Hivernal mixture, Linalyl acetate, Citronellyloxyacetaldehyde, Delta-Muscenone, Romanolide, beta-Pinene, Karanal, Vertenex, o-tert-Butylcyclohexyl acetate (verdox), Nectaryl, gamma-Decalactone, Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, Dodecanal, Eucalyptol, Rose oxide, undecanal (undecyl aldehyde), Allyl caproate, Romascone, Allyl heptanoate, a-Irone, Hexyl acetate, Liffarome, Vertoliff, anisic aldehyde, gamma methyl ionone, Nonanal, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E, 6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, Benzaldehyde, Neobutenone, triplal or ligustral, 10-Undecenal, Citronellal, N-Decanal, Vanillin, L-Carvone, Isocyclocitral, Octanal, Methyl benzoate, phenyl ethyl acetate, Citral, Indole, and mixtures thereof.

Other suitable perfume raw materials that can be used in the present application may also include the following: Stemone, Cashmeran, GERANIOL, Citronellyl nitrile, Linalool, Ethyl linalool, Benzyl acetate, Undecavertol, Methyl Phenyl Carbinyl Acetate, 6-Nonen-1-ol, (6Z)-, Benzyl propionate, Iso-E Super, 2,6-Nonadien-1-ol, (2E,6Z)-(10% Nonadienol in DPG), cis-3-Hexen-1-ol (beta gamma hexenol), Isobornyl acetate, Ambrox DL, ozone propanal (Floralozone), 3-methyl-5-(2,2,3-trimethyl-3-cyclopenten-1-yl) pent-4-en-2-ol (Ebanol), Phenethyl isobutyrate, Florhydral, phenyl ethyl alcohol, bourgeonal, gamma-Undecalactone_ (racemic), Dihydromyrcenol, Ethyl_2-methyl-1,3-dioxolane-2-acetate (Fructone), Bigarade oxide, Allyl cyclohexyl propionate, Tetrahydrolinalool (Tetrahydro Linalool), Trimofix O, Citronellol, Neofolione, Hivernal mixture, Linalyl acetate, Citronellyloxyacetaldehyde, Delta-Muscenone, Romanolide, beta-Pinene, Karanal, Vertenex, o-tert-Butylcyclohexyl acetate (verdox), Nectaryl, gamma-Decalactone, Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, Dodecanal, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, Nonanal, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, Benzaldehyde, Neobutenone, triplal or ligustral, 10-Undecenal, Citronellal, N-Decanal, Vanillin, L-Carvone, Isocyclocitral, Octanal, Methyl benzoate, phenyl ethyl acetate, Citral, Indole, and mixtures thereof.

Additional suitable perfume raw materials that can be used in the present application may include the following: Isoeugenol, Heliotropin, Oxalone (Calone 1951), Cinnamic aldehyde, Dihydro-beta-ionone, Ethyl acetate, cyclemax, Eugenol, d-Limonene, Vivaldie, Cyclogalbanate, trans-Anethole, anethole, cis-3-Hexenyl butyrate, Flor acetate, Violiff, Aurantiol, Damascenone, trans-Pinoacetaldehyde, Dodecanal, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, Nonanal, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl Pamplemousse, methyl ionone (Xandralia), Violiff, Aurantiol, Damascenone, trans-Pinoacetaldehyde, Dodecanal, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, Nonanal, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E, 6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, Benzaldehyde, Neobutenone, triplal or ligustral, 10-Undecenal, Citronellal, N-DECANAL, Vanillin, L-Carvone, Isocyclocitral, Octanal, Methyl benzoate, phenyl ethyl acetate, Citral, Indole, and mixtures thereof.

Further suitable perfume raw materials that can be used in the present application may include the following: Violiff, Aurantiol, Damascenone, trans-Pinoacetaldehyde, Dodecanal, Eucalyptol, Rose oxide, Undecanal (Undecyl Aldehyde), Allyl caproate, Romascone, Allyl heptanoate, a-Irone, Hexyl acetate, Liffarome, Vertoliff, anisic aldehyde, gamma methyl ionone, Nonanal, Frutene, allyl amyl glycolate, Methyl 2-octynoate, beta-Ionone, Ethyl Oenanthate, Maltol, alpha-Damascone, Methyl-2-nonynoate, gamma-Nonalactone, Dimetol, Methyl Pamplemousse, methyl ionone (Xandralia), 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E,6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, Benzaldehyde, Neobutenone, triplal or ligustral, 10-Undecenal, Citronellal, N-Decanal, Vanillin, L-Carvone, Isocyclocitral, Octanal, Methyl benzoate, phenyl ethyl acetate, Citral, Indole, and mixtures thereof.

Additionally, suitable perfume raw materials that can be used in the present application may include the following: 2-Nonen-1-al, Oxane, (E)-2,(Z)-6-Nonadienal, Trans-2-Hexenal, ethyl butyrate, Prenyl acetate, Ethyl-2-methylbutyrate, Melonal, Isoamyl acetate, 2,6-Nonadien-1-ol, (2E, 6Z)-(Nonadienol), 10% Labienone Oxim (labienoxime) in DPG, Ethyl Caproate, Phenylacetaldehyde, isobutyl quinoline, manzanate, 2-Methylundecanal, Methyl anthranilate, cis-3, cis-6-nonadienol, Ethyl vanillin, Benzaldehyde, Neobutenone, triplal or ligustral, 10-Undecenal, Citronellal, N-Decanal, Vanillin, L-Carvone, Isocyclocitral, Octanal, Methyl benzoate, phenyl ethyl acetate, Citral, Indole, and mixtures thereof.

Other suitable perfume raw materials can be found in the following U.S. Pat. Nos. 4,145,184; 4,209,417; 4,515,705; and 4,152,272. Still further, any other suitable perfume raw materials as known in the fragrancing arts may be utilized.

Still referring to FIG. 1, a wick 40 is in contact with the first and second compositions 30, 32 within the reservoir 26 and extends out of the container 22 through the neck 28. In some embodiments, a single wick 40 is utilized. Any suitable material as appreciated by one skilled in the art may be used for the wick. In some embodiments, the wick 40 may be made of either a hydrophilic material or a hydrophobic material. In an exemplary embodiment, the wick 40 may be made of a hydrophilic material.

Figure 2:
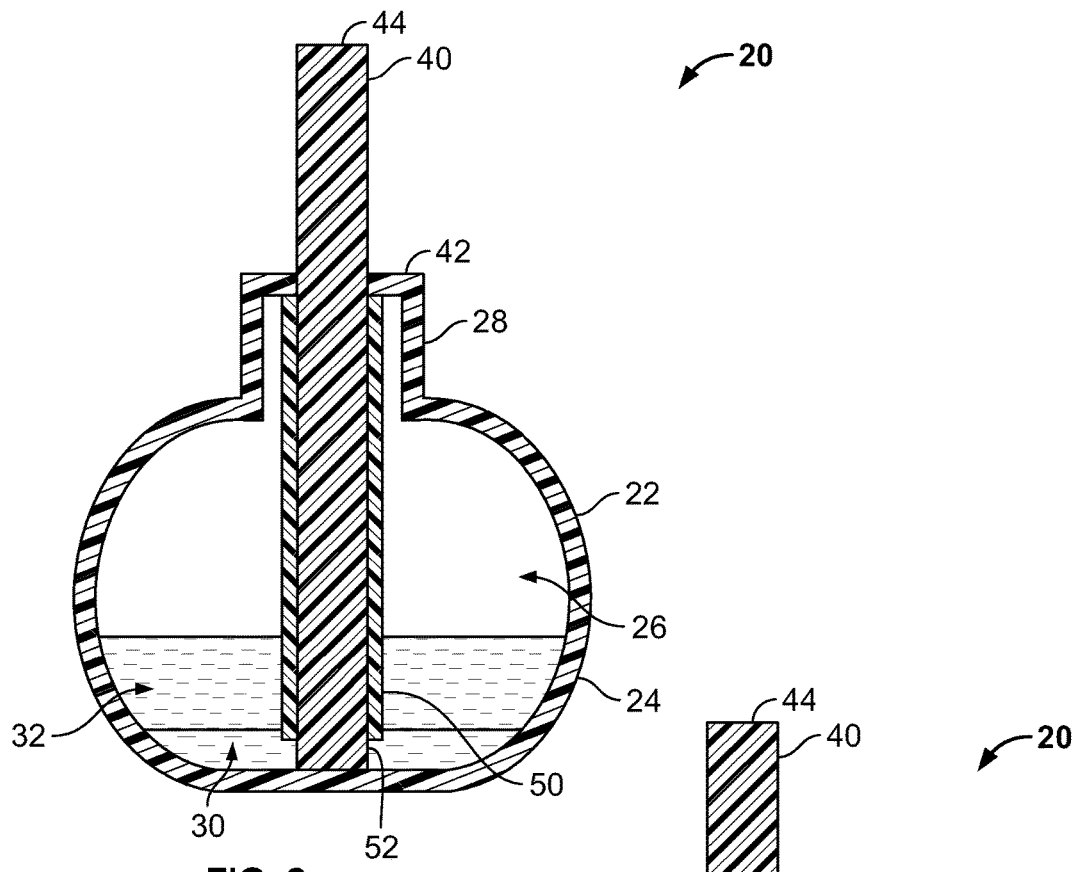
FIG. 2 is a cross-sectional view of the refill of FIG. 1, as the first composition is being depleted.
Figure 3:
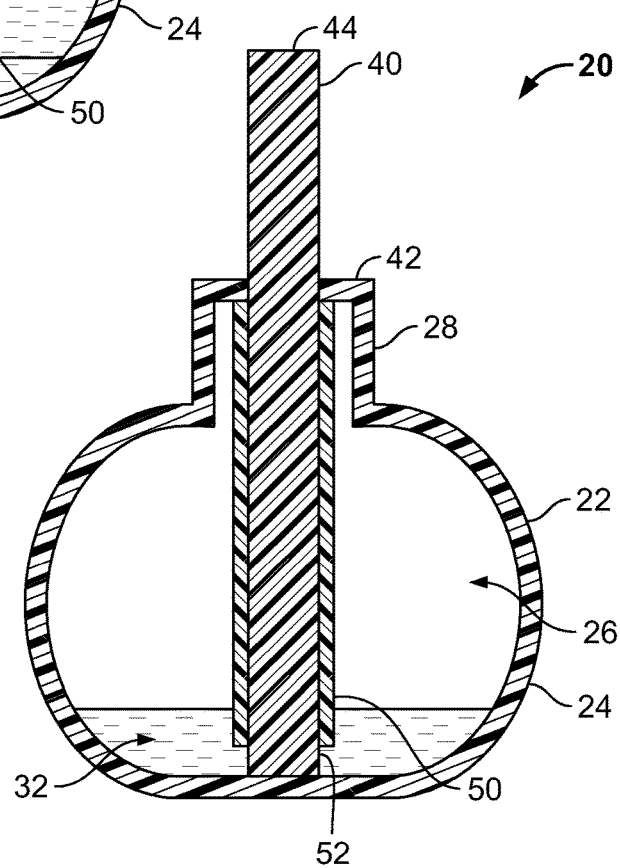
FIG. 3 is a cross-sectional view of the refill of FIG. 1, after the first composition has been fully depleted and as the second composition is being depleted.

A stopper or other retaining member 42 may be positioned within the neck 28 to position and retain the wick 40 within the container. The wick 40 may be made of any suitable porous material that is capable of wicking the first and second compositions 30, 32 to a top portion 44 of the wick 40 for emission into an area surrounding the refill 20. In an illustrative embodiment, the wick 40 is made of a sintered polyolefin material. A sheath 50 may be disposed about an entire perimeter of the wick 40 along a majority of a length of a portion of the wick 40 that is disposed within the reservoir 26. The sheath 50 may be formed of a plastic, metal, or any other suitable material, and may be impermeable to the first and second compositions 30, 32. In an illustrative example, as seen in FIG. 1, the sheath 50 may extend from the retaining member 42 to a point just above a bottom portion 52 of the wick 40. In other illustrative embodiments, the sheath 50 may extend to any point above an upper level 54 of the second composition 32. The bottom portion 52 of the wick 40 may be exposed so that the liquid compositions 30, 32 may move into and through the wick 40. In illustrative embodiments, the first composition 30 may be wicked through and emitted from the wick 40 first and, thereafter, the second composition 32 may be wicked through and emitted from the wick 40. While emission of the compositions 30, 32 is sequential, there may be some intermixing, and thus emission, of both of the compositions 30, 32 at the same time, for example, near the end of the first composition 30 and the beginning of the second composition 32. FIG. 2 depicts the refill 20 just prior to depletion of the first composition 30 and FIG. 3 depicts the refill after depletion of the first composition 30 and during emission of the second composition 32.

In some embodiments, Applicants envision that the second composition 32 may be wicked through and emitted from the wick 40 first and, thereafter, the second composition 30 may be wicked through and emitted from the wick 40. For example, the sheath 50 at the bottom portion 52 of the wick 40 may have a defined that allows on the liquid composition exposed to the bottom portion 52 of the wick 40 to enter the wick 40. In this embodiment, the second liquid composition 32 may move into and through the wick 40 first. Once the composition 32 is substantially depleted, the first composition 30 may be wicked through and emitted from the wick 40.

In illustrative embodiments, the first composition 30 is denser than the second composition 32 such that the first and second compositions 30, 32 form two distinct layers within the reservoir 26. In illustrative embodiments, the first composition 30 may be a water-based composition that contains one or more active ingredients, for example, a fragrance that comprises, e.g., one or more perfume raw materials, and the second composition 32 may be an oil-based fragranced composition. The second composition 32 may comprise one or more active ingredients, for example, one or more fragrances that comprise, e.g., one or more perfume raw materials.

In alternative embodiments, the first or second compositions 30, 32 may both be water-based or oil-based (with different densities) and/or one of the compositions 30, 32 may not include any active materials (for example, one composition may be water).

In some embodiments, the multi-phase compositions may further comprise an indication mechanism, e.g., an indicator, that can alert a user that one of the phases has been depleted. A suitable indication mechanism may include change of color, smell of odor, or any other indication mechanism that is appreciated by one skilled in the art.

For example, the second composition 32 may include an indicator that alerts a user that the first composition 30 has been depleted. In illustrative embodiments, the indicator may be a dye, for example, of any suitable color or colors. During emission of the first composition 30 from the delivery system and refill 20, the second composition 32 is visible to a user as a distinct, colored layer of liquid material. Once the first composition 30 is substantially depleted and the second composition 32 begins to move through the wick 40, the dye is also carried through the wick 40, thereby coloring the wick 40. The change in color of the wick 40 may indicate to a user the need to replace the delivery system and refill 20 or that the delivery system and refill is almost empty. In illustrative embodiments, the dye may not be soluble or capable of mixing with the first composition 30. In other illustrative embodiments, both compositions 30, 32 may include a dye or colorant, wherein when the first composition is emitted, a color in the wick may appear as a first distinct color. During a transition from the first composition 30 to the second composition 32, a color in the wick may appear as a mixture of the two colors. Further, as the first composition is completely depleted and the delivery system and refill is almost empty, a color in the wick may appear as a second distinct color. In a simple example, the first color may be red, the second color may be blue, and, during the transition, the wick may be colored various shades of purple.

In some embodiments, indicators of the present application may be compounds that are different from those used for fragrances in the different phases.

In other embodiments, indicators of the present application may be the same compounds as those used for fragrances in the different phases.

Figure 9:
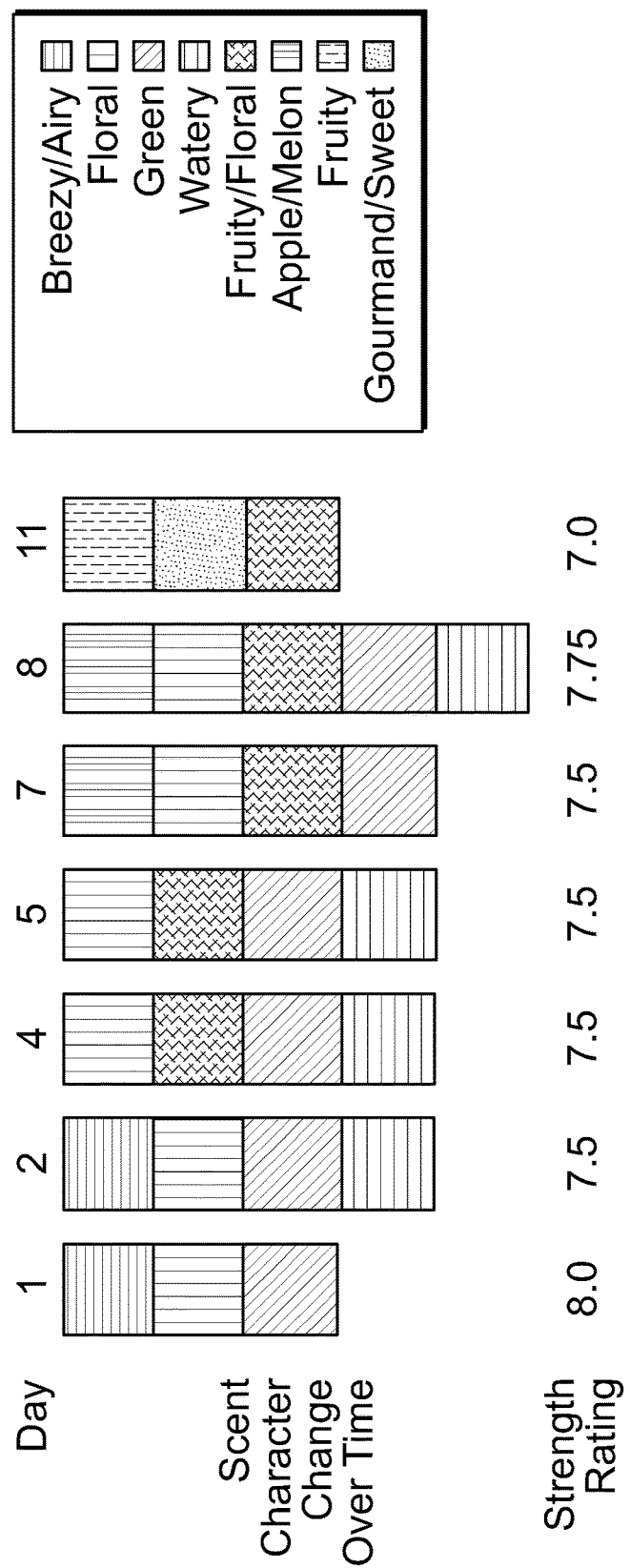
FIG. 9 is a graph depicting change in fragrance character from one layer of fragrance to the next in a sensory testing.

In alternative embodiments, the indicator may be a different active material in the second composition 32 than an active material contained in the first composition 30 and which, when activated, alerts a user to a condition within the delivery system and refill. By the term "activated," it is meant that the indicator may be sensed by a user such that the user becomes aware of a condition, for example, an empty or almost-empty refill. In an illustrative embodiment, the first composition 30 may be a water-based composition having a first active material with, for example, vanilla notes and the second composition 32 may be an oil-based composition having a second active material with, for example, floral notes. During emission of the first composition 30 from the delivery system and refill 20, the user may smell a distinct vanilla fragrance. Once the first composition 30 is substantially depleted and the second composition 32 begins to move through the wick 40, the indicator (i.e., a different odor) is activated, and the user may smell a distinct floral fragrance. The change in smell or odor is an indicator that the first composition 30 has been substantially depleted and the refill 20 needs to be replaced. While one specific example is disclosed, any number of different smells or odors may be utilized, as long as the difference in the active materials is enough to alert the user to a change in composition. FIG. 9 depicts change in fragrance character from one layer of the multi-phase composition to the next in a sensory test. FIG. 9 also depicts exemplary smells or odors of indicators that may be used in the present application.

In still alternative embodiments, the indicator may be the same active material at different intensity levels. The first and second compositions 30, 32 may be water and oil-based compositions, respectively, with the same or similar active materials with one of the first or second compositions 30, 32 having the active material(s) at a greater intensity level or strength. In an illustrative embodiment, the intensity level of the active material(s) in the second composition 32 may be greater than the intensity level of the active material(s) in the first composition 30. During emission of the first composition 30 from the delivery mechanism and refill 20, the user would sense the active material(s) at a normal level. Once the first composition 30 is substantially depleted and the second composition 32 begins to move through the wick 40, the indicator (i.e., a greater strength of an active material) may be activated and the active material(s) may be stronger such that the user senses a change in the level of the active material(s), thereby alerting the user to replace the refill 20 and also allowing the user to again sense a fragrance to which the user may have become habituated.

In other illustrative embodiments, the indicator may be both a dye and a different active material or intensity level in the first and second compositions 30, 32.

Figure 4:
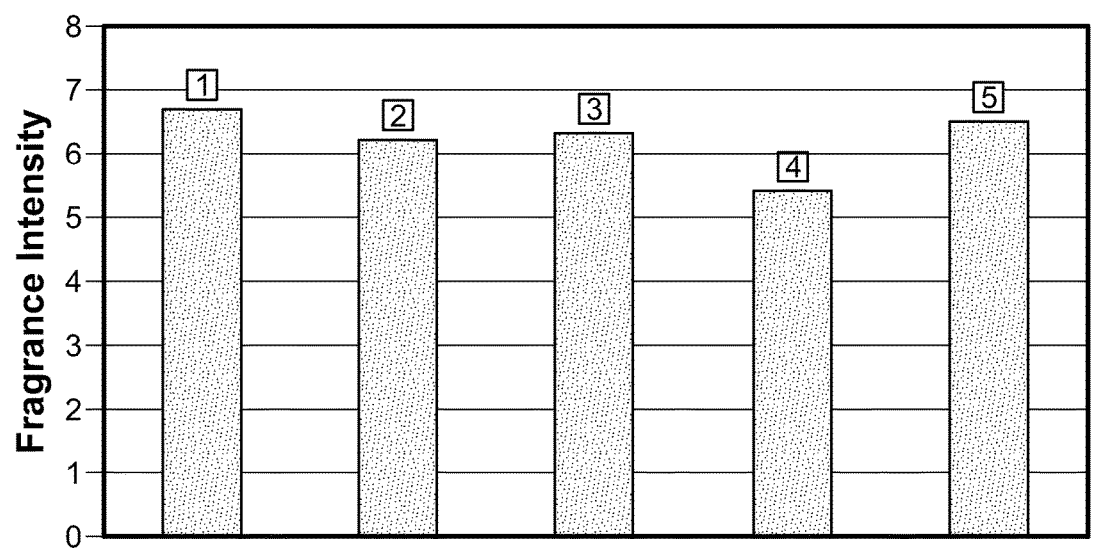
FIG. 4 is a graph depicting perceived fragrance intensity for various refills having water-based and/or oil-based fragrances.

FIG. 4 depicts perceived fragrance intensities for various delivery systems and refills in a trained sensory panel. Each of the individuals on the trained sensory panel was asked to rate perceived fragrance intensities on a scale of 0 to 15. In FIG. 4, Sample 1 is an oil-based fragrance delivered through a hydrophobic wick, Sample 2 is a water-based fragrance delivered first from a two-phase liquid, where an oil-based fragrance was the top layer, Sample 3 is a water-based fragrance delivered second from a 2-phase system that included an oil-based fragrance as the top layer, Sample 4 is a water-based fragrance delivered through a sintered polyolefin wick that has been treated with a hydrophilic surfactant prior to sintering, and Sample 5 is an oil-based fragrance delivered through a wick that has been treated with a hydrophilic surfactant prior to sintering.

Samples 4 and 5 show a difference in perceived intensities for a water-based fragrance (Sample 4) and an oil-based fragrance (Sample 5) having the same fragrance notes and delivered from the same type of wick. Samples 2 and 3 show that the perceived intensities for sequential oil and water-based fragrances are higher than a perceived intensity for a water-based fragrance alone (Sample 4), but lower than a perceived intensity for an oil-based fragrance alone (Sample 1).

Figure 5:
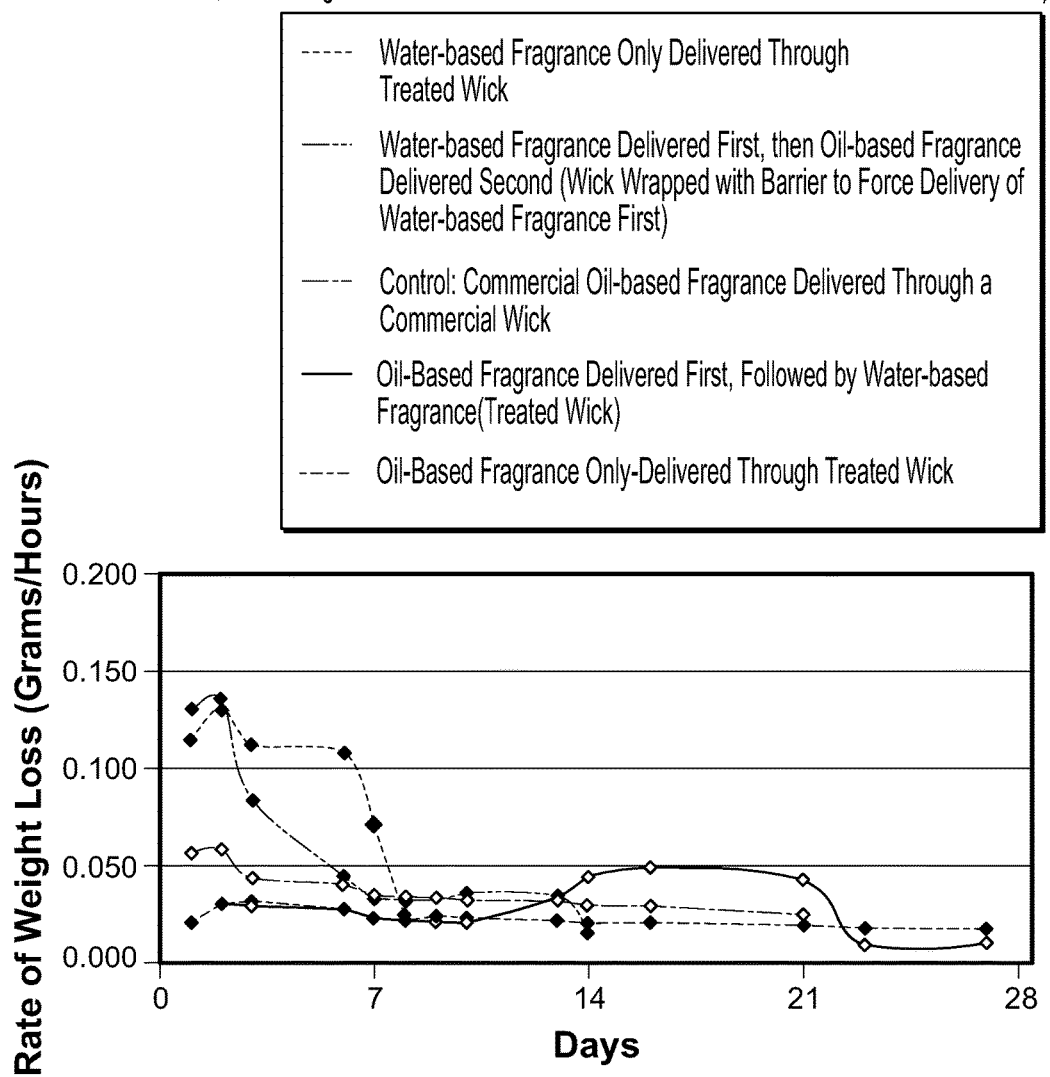
FIG. 5 is a graph depicting a rate of weight loss (in grams per hour) versus time for various compositions.

A graph depicting a rate of weight loss (in grams per hour) versus time is shown in FIG. 5. The graph depicts weight loss for (A) a water-based fragrance, (B) a first composition 30 that is a water-based fragrance, followed by a second composition 32 that is an oil-based fragrance, wherein the wick 40 was wrapped with a barrier layer 50 (see FIGS. 1-3) to force the compositions through the bottom portion 52 of the wick 40, (C) an oil-based fragrance delivered through an unmodified wick 40, (D) a first composition 32 that is an oil-based fragrance, followed by a second composition 30 that is a water-based fragrance, and (E) an oil-based fragrance delivered through a wick 40 that has been treated to make it hydrophilic, as described above.

The first and second compositions are delivered in sequence or in sequential order. Sequential order should not be constrained to mean that there is no mixing of the two phases (first and second compositions), but rather, sequential order means that over the life of the delivery system and refill, the liquid emitted from the wick varies from being substantially composed of one phase/composition at the beginning to substantially composed of another phase/composition at the end. Curve (B) in FIG. 5 depicts the delivery of mostly the water-based fragrance at first, which transitions to a delivery of mostly the oil-based fragrance near the end of the life of the liquid in the reservoir. Curve (D) in FIG. 5 depicts an upturn in the delivery rate at the end of the life of the liquid in the refill, which is caused by emitting mostly an oil-based fragrance followed by mostly a water-based fragrance. This upturn or increase in delivery provides an increase in noticeability of the fragrance (especially if different fragrances are used).

During the testing of FIG. 5, it was observed that water-based compositions move through wicks at a higher rate than oil-based compositions, but the wick will preferentially wick oil-based compositions before water-based compositions. The result is that, if an oil-based composition is to be emitted first, followed by a water-based composition, a barrier layer around the wick may not be necessary. Still further, (B) and (D) in FIG. 5 include the same two compositions with reversed order of emission.

In some embodiments of the present application, the material of the wick may be chosen in such a way that one phase composition would be absorbed and emitted first. In exemplary embodiments, a sheath may not be necessary for the wick of the present application.

Figure 6:
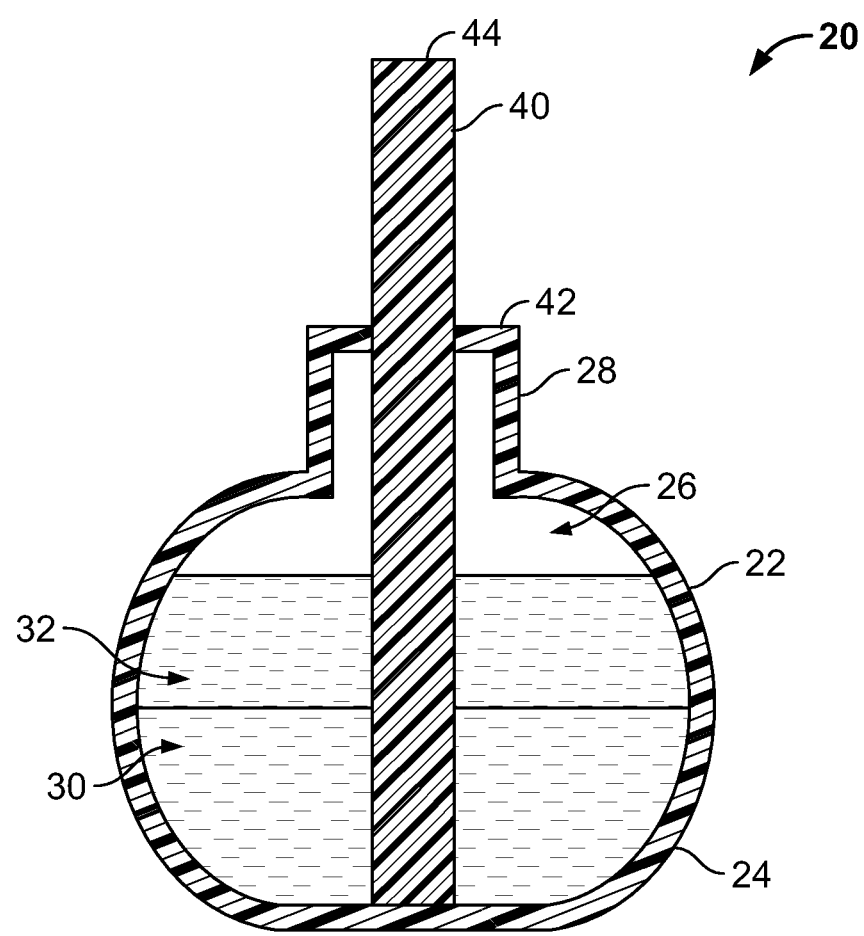
FIG. 6 is a cross-sectional view of a second embodiment of a refill including a container having a reservoir holding first and second compositions and a wick in contact with the first and second compositions and extending out of the refill.
Figure 7:
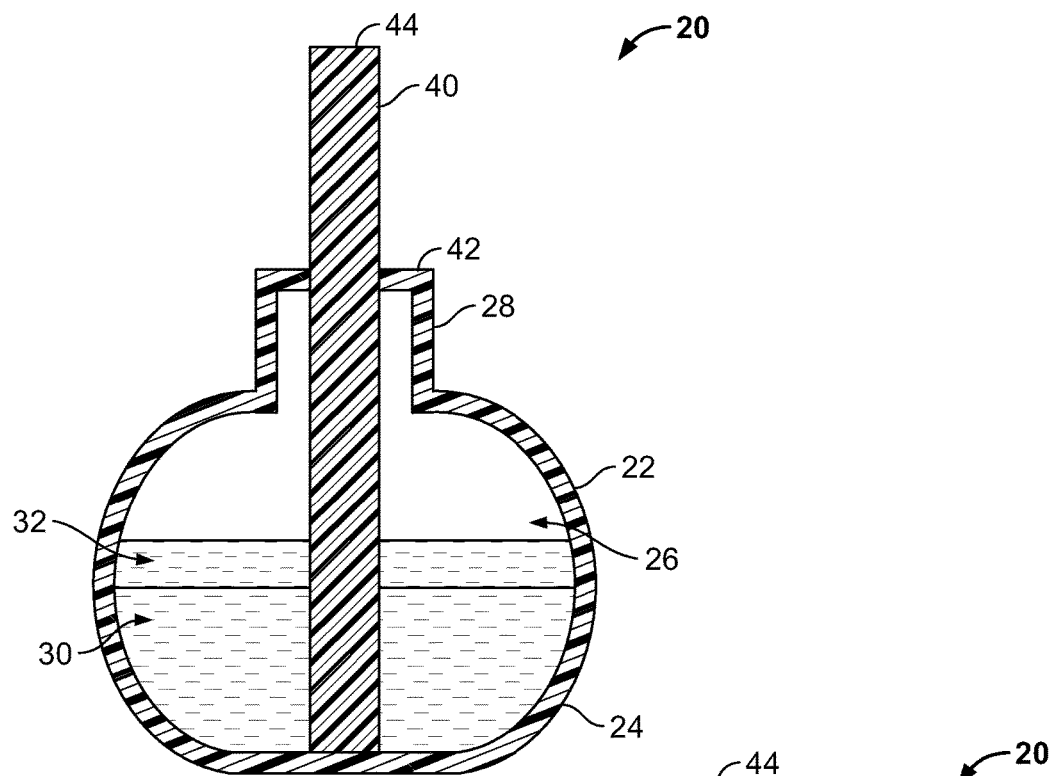
FIG. 7 is a cross-sectional view of the refill of FIG. 8, as the second composition is being depleted.
Figure 8:
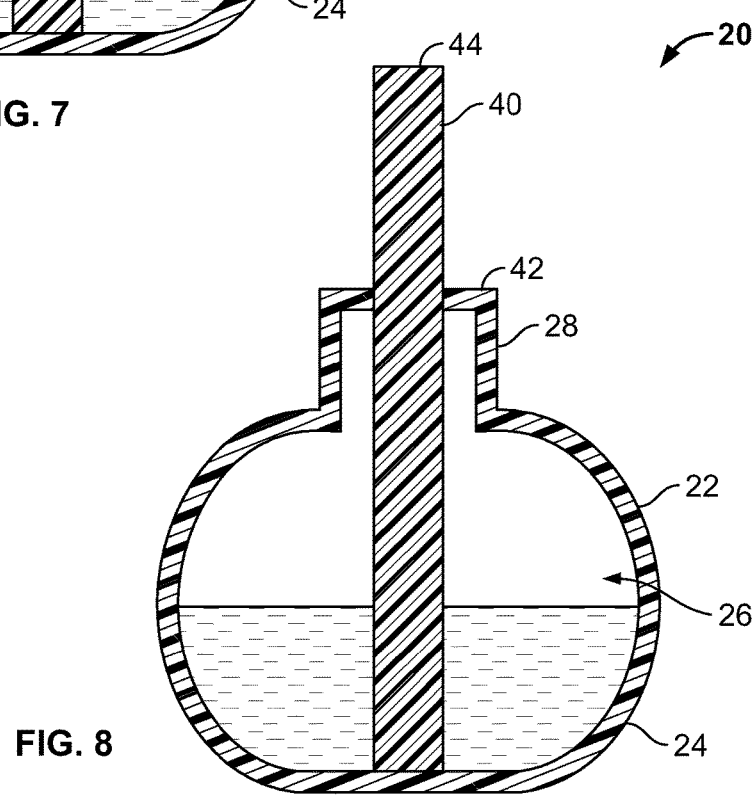
FIG. 8 is a cross-sectional view of the refill of FIG. 8, after the second composition has been fully depleted and as the second composition is being depleted.

Based on the results, as seen in FIG. 5, a second embodiment of a delivery system and refill 20 was developed, as depicted in FIG. 6. The delivery system and refill 20 of FIG. 6 is similar to the delivery system and refill of FIGS. 1-3, except that a sheath is not disposed over the wick 40. In illustrative embodiments, the first composition 30 is a water-based fragrance and the second composition 32 is an oil-based fragrance. As seen in FIGS. 7 and 8 and noted above, the wick 40 has an affinity for the second, oil-based composition 32 and, therefore, absorbs and emits the second composition 32 first (FIG. 7). Once the second composition 32 has been substantially depleted, as seen in FIG. 8, the first composition 30 is absorbed and emitted by the wick 40.

Any of the indicators, as described above with respect to the first embodiment and FIGS. 1-3, may be utilized with the third embodiment. The indicators may be implemented and may function in the same manner as described above.

It may be important in determining fragrances or aroma chemicals for each of the compositions to be used in the refills disclosed herein, to consider fragrances for each phase or composition that stay in that phase and do not migrate to other phase(s). While perfect containment of fragrances within their phases may not be possible, selection of fragrances may be made that may bias a fragrance to one phase or another. In an illustrative embodiment, all of the fragrance components may be chosen for the water-based phase with a CLogP of 2 or less such that the fragrance components have a great affinity for the water phase. Likewise, all of the fragrance components may be chosen for the oil-based phase with a CLogP of 3 or more such that the fragrance components have a greater affinity for the oil phase.

In one embodiment, the present application discloses delivery systems and refills for delivering and emitting multi-phase compositions in a phase-by-phase manner. In exemplary embodiments, the delivery systems and refills of the present application allow a perfumer to design a fragrance on the basis of solubility parameters of fragrance components along with volatility of the components.

In some embodiments of the present application, one may develop a fragrance composition where the most volatile components in the compositions are more soluble in the top layer of the multi-phase composition.

In other embodiments of the present application, one may develop a fragrance composition where the more volatile components of the compositions are better solubilized in the bottom layer of the multi-phase composition.

In further embodiments of the present application, one may develop a fragrance composition where the least volatile fragrance components in a multi-phase composition are exhausted more quickly from the delivery system than the more volatile components in the composition.

For example, a two-phase fragrance composition as shown in FIGS. 1-8, delivered sequentially, may provide a user unique fragrance experiences that are not available to him/her with conventional, single-phase fragrance compositions. Specifically, one may formulate a fragrance composition for the bottom layer with perfume raw materials that have low ClogP values and relatively low volatility (as illustrated by the perfume raw materials circled in the scatter plot in FIG. 10). In a conventional single-phase fragrance composition, these perfume raw materials would evaporate after the more volatile perfume raw materials on the scatter plot. In certain embodiments of the present application, these materials may be emitted at a faster rate than many of the more volatile perfume raw materials that have high ClogP values.

In some embodiments of the present application, a multi-phase composition is a two-phase composition. The two-phase composition comprises one water phase and one oil phase. The term "water phase," as used herein, refers to a phase in which water (and/or a water-soluble solvent) is a primary carrier. The term "oil phase," as used herein, refers to a non-aqueous phase in which a water-insoluble solvent (e.g., an organic solvent) is the primary carrier.

In some embodiments, the amount of water is from about 5% to about 20% by weight of the multi-phase composition, from about 8% to about 15% by weight of the multi-phase composition, from about 9% to about 14% by weight of the multi-phase composition, or from about 10% to about 12% by weight of the multi-phase composition.

Figure 11:
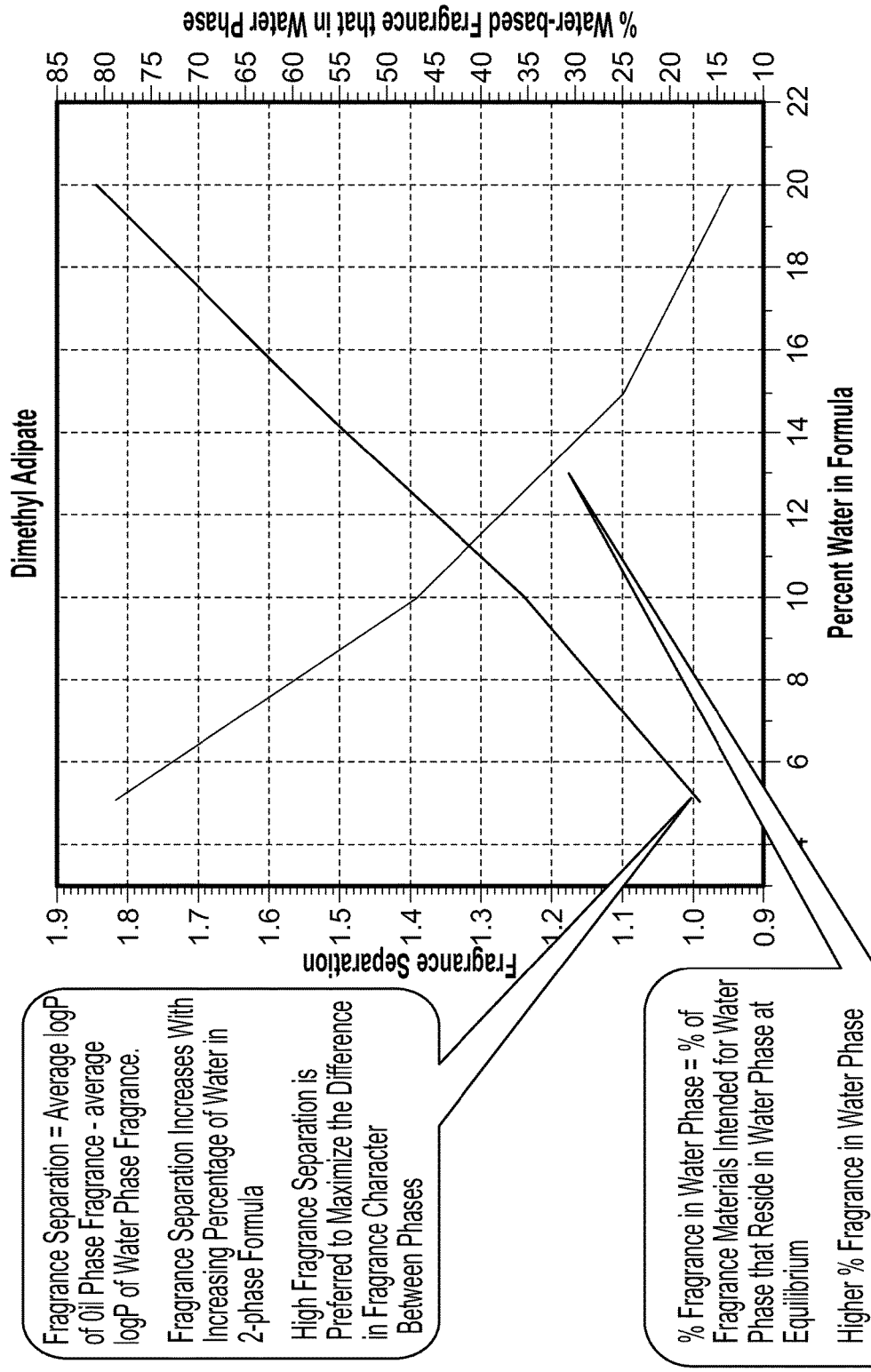
FIG. 11 is a graph depicting that an optimal amount of water in a 2-phase system determined by computational chemistry exists at about 10 to 12% water.
Figure 12:
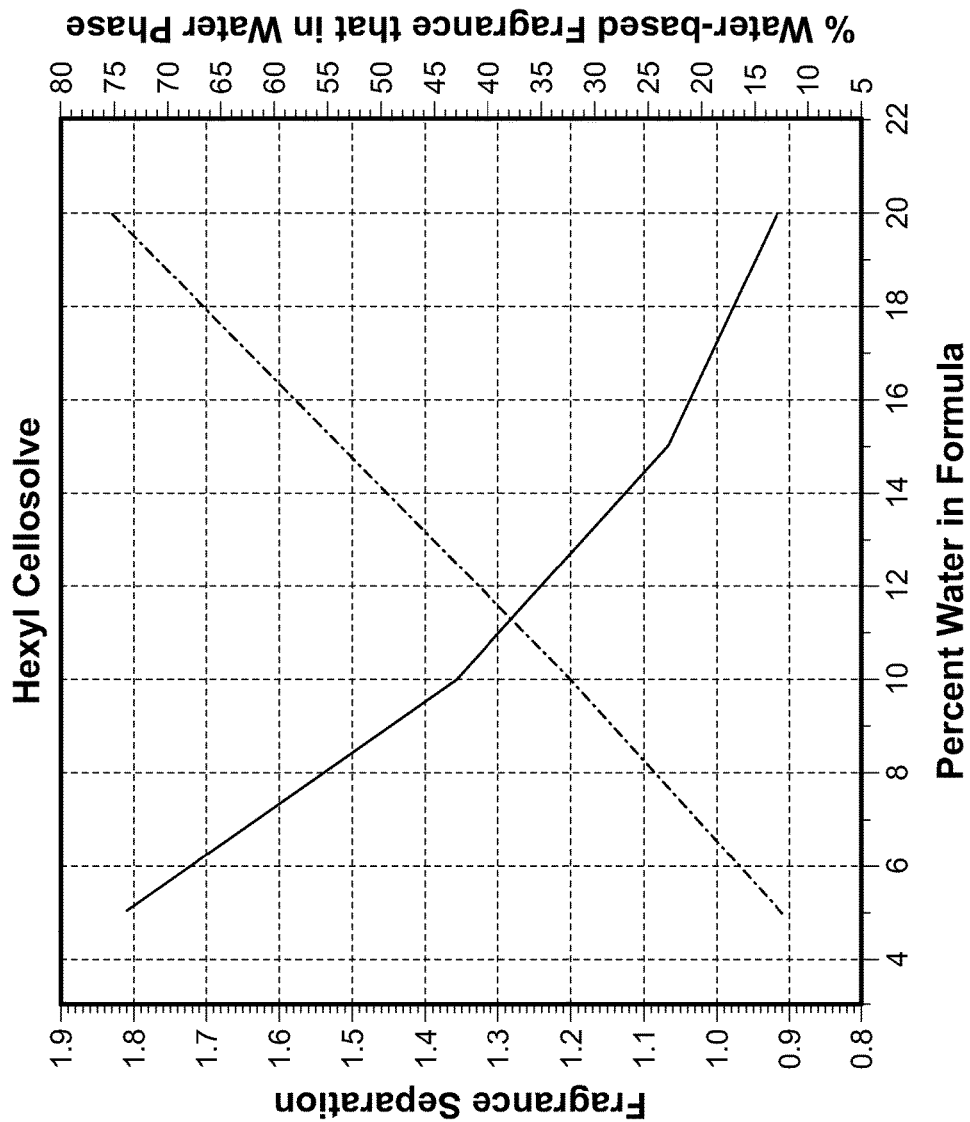
FIG. 12 is a graph depicting that an optimal amount of water in a 2-phase system determined by computational chemistry exists at about 10 to 12% water.

FIG. 11 depicts that an optimal amount of water in a 2-phase system determined by computational chemistry exists at about 10% to about 12% water by weight with dimethyl Adipate as a primary oil phase solvent. FIG. 12 depicts that an optimal amount of water in a 2-phase system determined by computational chemistry exists at about 10% to about 12% water by weight with hexyl cellosolve as a primary oil phase solvent. Applicants note that the computational result in hexyl cellosolve is similar to that in dimethyl adipate.

In some embodiments of the present application, the amount of the water phase fragrance in the multi-phase composition is from about 12% to about 28% by weight, from about 13% to about 27% by weight, or from about 15% to about 25% by weight.

The solvent of the water phase may include, but are not limited to, water, alcohols (e.g., methanol, ethanol), DMSO, acetone, water-soluble diols or triols such as ethylene glycol, propylene glycol or glycerol and others. In some embodiments, the solvent of the water phase may include propylene glycol and water.

In some embodiments, the amount of water phase solvent in the two-phase composition is from about 18% to about 39% by weight, from about 19% to about 38% by weight, or from about 20% to about 35%.

In some embodiments, the amount of the oil phase fragrance in the multi-phase composition is from about 10% to about 30% by weight, from about 12% to about 28% by weight, or from about 15% to about 25% by weight.

The solvent of the oil phase may be selected from, but not limited to, one or more of methylene chloride, ethyl acetate, benzyl alcohol, acetone, acetic acid, propylene carbonate, dichloromethane, chloroform, 1,4-dioxane, dimethylformamide (DMF), toluene, tetrahydrofuran (THF), dimethyl adipate, isopar M, hexyl cellosolve, and other organic solvents. In one embodiment, the solvent of the oil phase may be dimethyl adipate, isopar M (or a solvent with similar chemical structure) or hexyl cellosolve. In an exemplary embodiment, the solvent of the oil phase is isopar M.

In one embodiment, the solvent of the oil phase may include isopar M and another organic solvent.

In one embodiment, the other organic solvent may be hexyl cellosolve or dimethyl adipate. Preferably, the other solvent is hexyl cellosolve. Applicants note that the addition of a second oil phase solvent tends to increase overall delivery rates, and increase peak delivery rate for the water phase. In one specific embodiment, the addition of dimethyl adipate increases overall delivery rates, and increases peak delivery rate for the water phase. Further, hexyl cellosolve is a better solvent than dimethyl adipate for increasing overall delivery rates, and increasing peak delivery rate for the water phase.

In some embodiments, the amount of the oil phase solvent in the multi-phase composition is from about 7% to about 25% by weight, from about 8% to about 23% by weight, or from about 10% to about 20% by weight.

In an exemplary embodiment, the multi-phase composition is comprised of between about 10 and about 20% by weight oil phase solvent including at least Isopar M, between about 15 and about 25% by weight oil phase fragrance, between about 20 and about 35% by weight water phase solvent including propylene glycol, between about 15 and about 25% by weight water phase fragrance, and between about 10 and about 12% by weight water.

Figure 13:
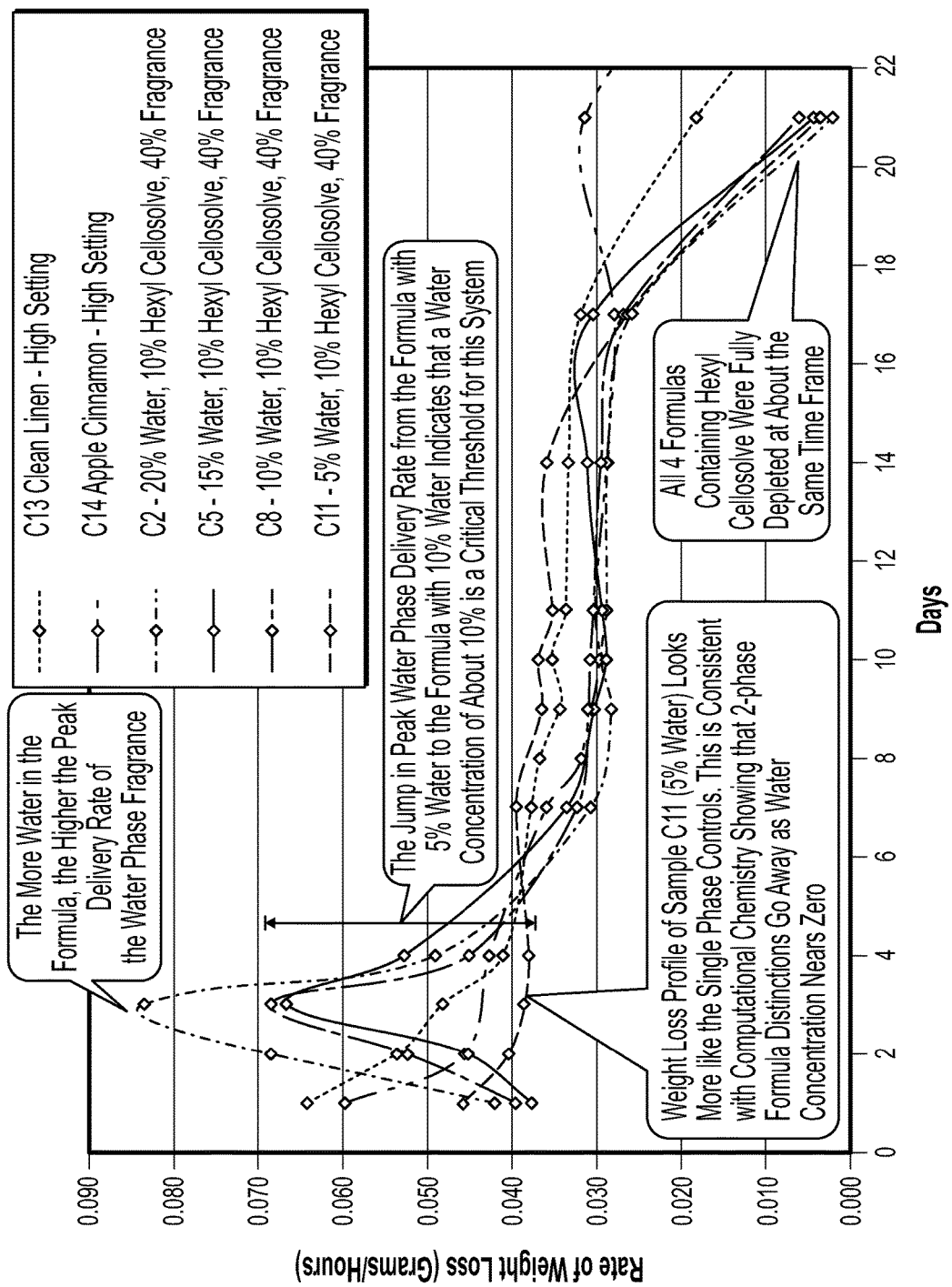
FIG. 13 is a graph depicting a comparison of different two-phase formulas containing hexyl cellosolve as one of two oil phase solvents and Isopar M as another oil phase solvent.

FIG. 13 depicts a comparison of time-dependent weight loss of different 2-phase compositions containing hexyl cellosolve as one of the two oil phase solvents. Isopar M was used as the other oil phase solvent. Sample 13 includes clean linen as the sole active ingredient (on a high output setting). Sample 14 includes apple cinnamon as the sole active ingredient (on a high output setting). The detailed components for samples C2, C5, C8 and C11 are listed in FIGS. 19 and 20.

The data of C2, C5, C8 and C11 in FIG. 13 shows that the more water in the formula, the higher the peak delivery rate of the water phase fragrance. The jump in peak water phase delivery rate from the formula with 5% water (i.e., C11) to the formula with 10% water (i.e., C8) indicates that a water concentration of about 10% is an important threshold for the present delivery system and refill. Applicants note that the weight loss profile of sample C11 (i.e., 5% water) is similar to those of the single phase controls (samples C13 and C14). This observation is consistent with computational chemistry results (i.e., FIGS. 11 and 12) showing that the 2-phase composition distinctions disappear as the water concentration nears zero. Applicants note that all four compositions of C2, C5, C8 and C11 containing hexyl cellosolve were fully depleted at about the same time frame.

Figure 14:
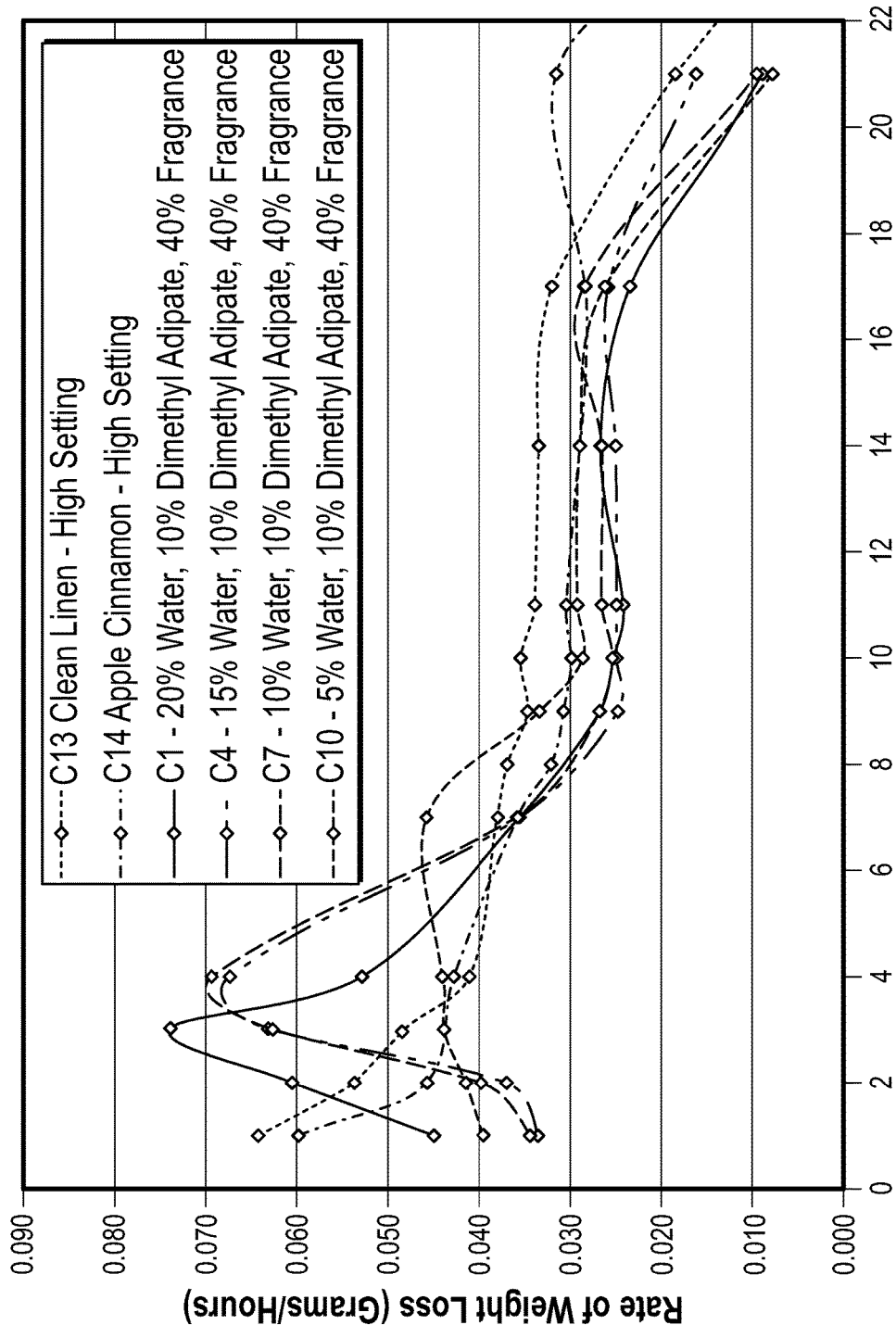
FIG. 14 is a graph depicting a comparison of 2-phase formulas containing dimethyl adipate as one of two oil phase solvents and Isopar M as another oil phase solvent.

FIG. 14 depicts a comparison of time-dependent weight loss of different 2-phase compositions containing dimethyl adipate as one of the two oil phase solvents. Isopar M was used as the other oil phase solvent. Sample 13 includes clean linen as the sole active ingredient (on a high intensity setting). Sample 14 includes apple cinnamon as the sole active ingredient (on a high intensity setting). The detail components for samples C1, C4, C7 and C10 are listed in FIGS. 19 and 20.

As shown in FIG. 14, the delivery rates of all 2-phase formulas (samples C1, C4, C7 and C10) in Day 1 and Day 2 are lower than those of controls (samples C13 and C14).

Applicants envision in certain embodiments of the present application, a consumer may need a fragrance that is not be "too strong" at first. In some embodiments of the present application, a fragrance's intensity may be perceived as more consistent in the first week as fragrance delivery ramps-up. Further, Applicants note that oil phase delivery rates for formulas containing dimethyl adipate (i.e., samples C1, C4, C7 and C10) trend below the two controls (samples C13 and C14) after the first week of delivery. In comparison, FIG. 13 shows that formulas containing hexyl cellosolve (samples C1, C4, C7 and C10) trend near the delivery rate of C14 (i.e., Apple Cinnamon) after the first week of delivery.

Figure 15:
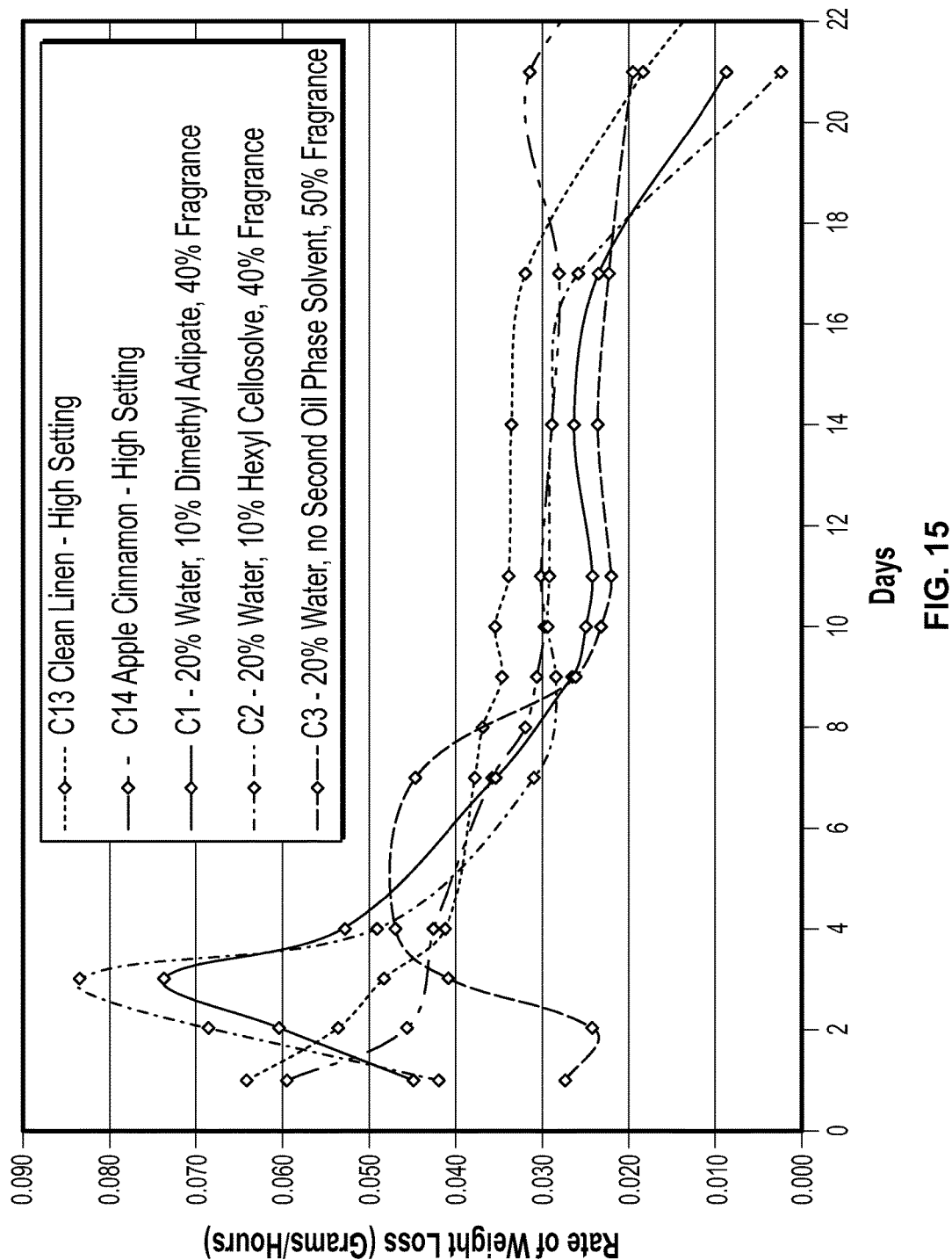
FIG. 15 is a graph depicting a comparison of 2-phase formulas containing 20% water as one of two water phase solvents and propylene glycol as another water phase solvent.

FIG. 15 depicts a comparison of 2-phase formulas containing 20% water as one of the two water phase solvents. Propylene glycol was used as the other water phase solvent. Sample 13 includes clean linen as the sole active ingredient. Sample 14 includes apple cinnamon as the sole active ingredient. The detailed components for samples C1, C2 and C3 are listed in FIGS. 19 and 20.

As shown in FIG. 15, addition of a second oil phase solvent (e.g., hexyl cellosolve or dimethyl adipate) enhances overall delivery rate: hexyl cellosolve>dimethyl adipate>no second oil phase solvent.

In one embodiment, when isopar M is used as one of the oil phase solvents, the two-phase composition may include a second oil phase solvent. In an exemplary embodiment, the second oil phase solvent may be hexyl cellosolve or dimethyl adipate.

Figure 16:
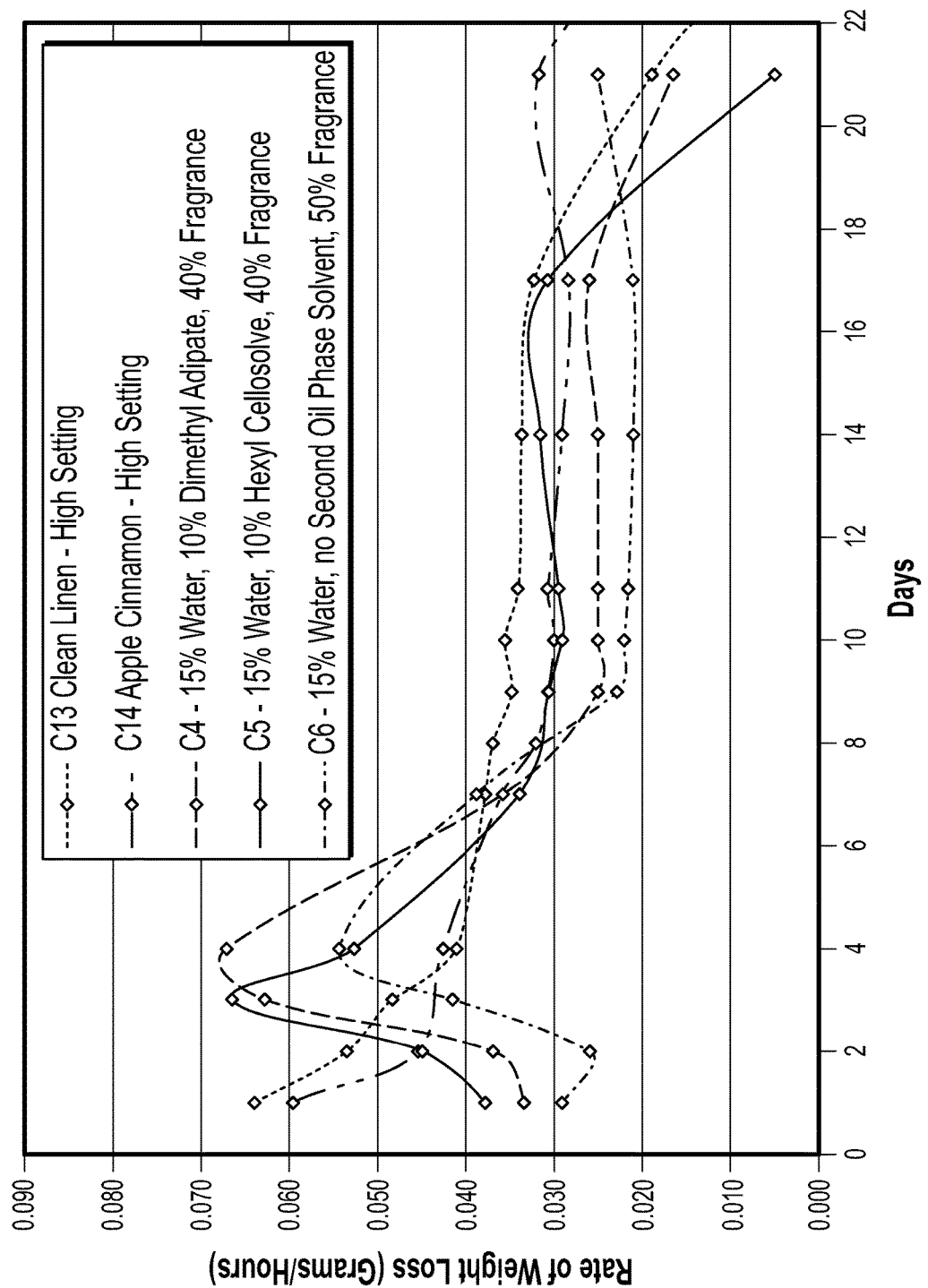
FIG. 16 is a graph depicting a comparison of 2-phase formulas containing 15% water as one of two water phase solvents and propylene glycol as another water phase solvent.

FIG. 16 depicts a comparison of 2-phase formulas containing 15% water as one of the two water phase solvents. Propylene glycol was used as the other water phase solvent. Sample 13 includes clean linen as the sole active ingredient. Sample 14 includes apple cinnamon as the sole active ingredient. The detail components for ss C4, C5 and C6 are listed in FIGS. 19 and 20.

Similar to FIG. 15, FIG. 16 shows that even when the water concentration decreases from 20% (e.g., samples C1, C2 and C3) to 15% by weight (e.g., samples C4, C5 and C6), addition of a second oil phase solvent (e.g., hexyl cellosolve or dimethyl adipate) enhances overall delivery rate.

Figure 17:
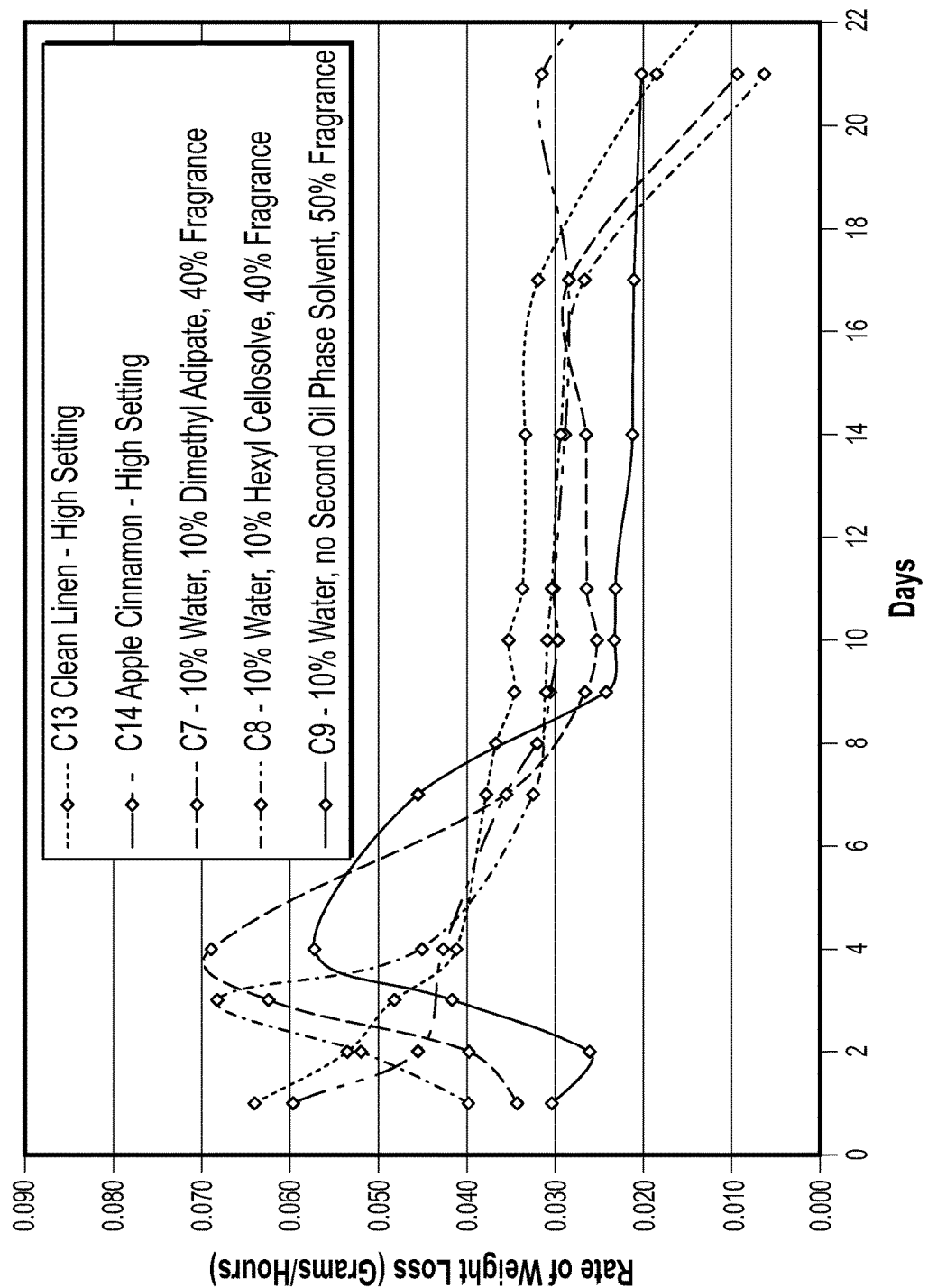
FIG. 17 is a graph depicting a comparison of 2-phase formulas containing 10% water as one of two water phase solvents and propylene glycol as another water phase solvent.

FIG. 17 depicts a comparison of 2-phase formulas containing 10% water as one of the two water phase solvents. Propylene glycol was used as the other water phase solvent. Sample 13 includes clean linen as the sole active ingredient. Sample 14 includes apple cinnamon as the sole active ingredient. The detailed components for the samples C7, C8 and C9 are listed in FIGS. 19 and 20.

Similar to FIGS. 15 and 16, FIG. 17 shows that even when the water concentration decreases from 20% (e.g., the samples C1, C2 and C3) or 15% by weight (e.g., samples C4, C5 and C6) to 10% (e.g., samples C7, C8 and C9), the addition of a second oil phase solvent (e.g., hexyl cellosolve or dimethyl adipate) enhances overall delivery rate.

Figure 18:
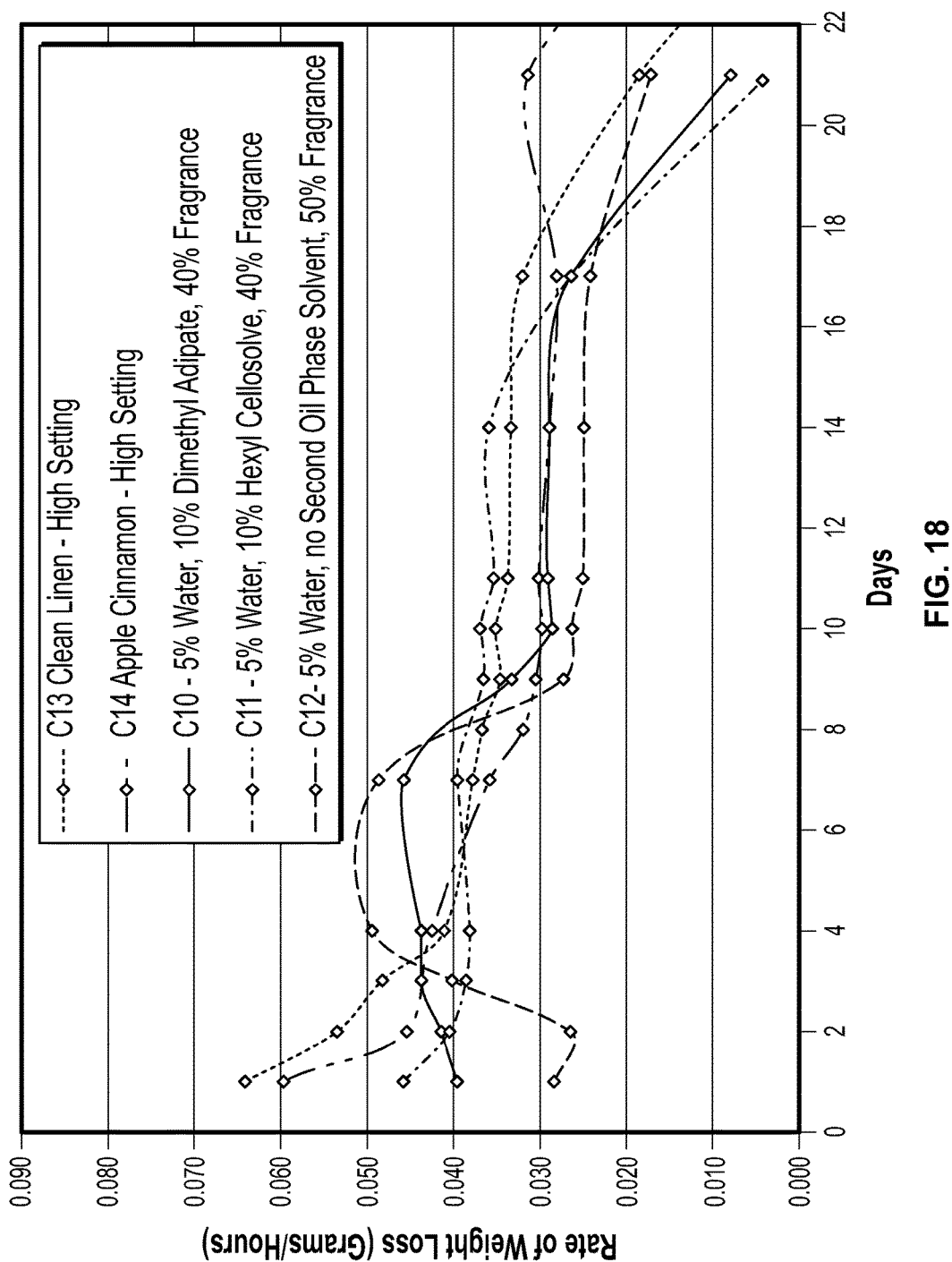
FIG. 18 is a graph depicting a comparison of 2-phase formulas containing 5% water as one of two water phase solvents and propylene glycol as another water phase solvent.

FIG. 18 depicts a comparison of 2-phase formulas containing 5% water as one of two water phase solvents. Propylene glycol was used as the other water phase solvent. Sample 13 includes clean linen as the sole active ingredient. Sample 14 includes apple cinnamon as the sole active ingredient. The detail components for samples C10, C11 and C12 are listed in FIGS. 19 and 20.

FIG. 18 shows that, when the water concentration is about 5% by weight (e.g., the samples C10, C11, and C12), the composition differences from one phase to the next has diminished. As such, shape of weight loss profiles in FIG. 18 provides evidence that formula composition changes from one phase to the next phase.

Further, Applicants note that addition of a second oil phase solvent when water concentration is about 5% by weight allows the two phases to blend. This observation also suggested by the weight loss profiles is consistent with the results as predicted in computational chemistry (See, e.g., FIGS. 11 and 12).

While the illustrative embodiments described in detail herein include only two compositions, the principles of the present application may be applied to any number of the same and/or different compositions. If the compositions are to be emitted in a sequential order, the compositions may have different densities such that each individual composition will be substantially emitted before the next composition begins. In an illustrative embodiment in which more than two compositions are utilized, the phases could include a water phase, a non-polar solvent phase, and a thickened liquid or gel phase.

Any of the refills, compositions, methods, and/or indicators described in detail herein may be utilized within any passive or active dispenser or alone. Exemplary active dispensers in which the refills, compositions, and/or indicators may be utilized include, but are not limited to, those including one or more of a fan, a heater, a piezoelectric actuator, or any other suitable actuator.

Any of the embodiments described herein may be modified to include any of the structures or methodologies disclosed in connection with other embodiments.

Further, although directional terminology, such as front, back, top, bottom, upper, lower, etc. may be used throughout the present specification, it should be understood that such terms are not limiting and are only utilized herein to convey the orientation of different elements with respect to one another.

All documents cited in the Detailed Description are, in relevant part, incorporated herein by reference; the citation of any document is not to be construed as an admission that it is prior art with respect to the present disclosure.

INDUSTRIAL APPLICABILITY

The present disclosure provides delivery systems and refills containing multiple compositions for sequential emission, which may increase the noticeably of one or more fragrances emitted from the delivery systems and refills. The present disclosure also provides delivery systems, refills, compositions, and methods for indicating a condition within the refill, for example, that a composition has been substantially depleted from a delivery system and refill.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

I claim:

1. A multi-phase fragrance composition to be delivered from a container having a body forming a reservoir and an opening in communication with the reservoir, the multi-phase fragrance composition being disposed within the reservoir, and a single wick being in contact with the multi-phase fragrance composition to sequentially emit different phases of the multi-phase fragrance composition, the multi-phase composition comprising:

a water phase composition and an oil phase composition, wherein the water phase composition and the oil phase composition are substantially separated, and the water phase composition has a different fragrance characteristic than the oil-phase composition, wherein the water phase composition comprises
- a water phase fragrance; and
- both water and propylene glycol as water phase solvents;

the oil phase composition comprises
- an oil phase fragrance; and
- a hydrocarbon solvent as an oil phase solvent, wherein the hydrocarbon solvent comprises alkanes, C11-C16 isoalkanes, and cycloalkanes.

2. The multi-phase fragrance composition of claim 1, wherein the water concentration of the multi-phase composition is between about 5% and about 20% by weight.

3. The multi-phase fragrance composition of claim 2, wherein the water concentration of the multi-phase composition is between about 8% and about 15% by weight.

4. The multi-phase fragrance composition of claim 3, wherein the water concentration of the multi-phase composition is between about 10% and about 12% by weight.

5. The multi-phase fragrance composition of claim 1, wherein the water phase fragrance concentration is between about 15% and about 25% by weight of the multi-phase composition.

6. The multi-phase fragrance composition of claim 5, wherein the water phase solvent concentration is between about 20% and about 35% by weight of the multi-phase composition.

7. The multi-phase fragrance composition of claim 1, wherein the oil phase composition comprises one additional oil phase solvent selected from dimethyl adipate and hexyl cellosolve.

8. The multi-phase fragrance composition of claim 1, wherein the oil phase fragrance concentration is between about 15% and about 25% by weight of the multi-phase composition.

9. The multi-phase fragrance composition of claim 8, wherein the oil phase solvent concentration is between about 10% and about 20% by weight of the multi-phase composition.

10. The multi-phase fragrance composition of claim 1, wherein the wick is made of either a hydrophilic material or a hydrophobic material.

11. The multi-phase fragrance composition of claim 1, wherein:
- the water concentration of the multi-phase composition is between about 10% and about 12% by weight of the multi-phase composition;
- the water phase fragrance concentration is between about 15% and about 25% by weight of the multi-phase composition,
- the water phase solvent concentration is between about 20% and about 35% by weight of the multi-phase composition;
- the oil phase fragrance concentration is between about 15% and about 25% by weight of the multi-phase composition; and
- the oil phase solvent concentration is between about 10% and about 20% by weight of the multi-phase composition.

* * * * *